United States Patent [19]
Holsinger et al.

[11] Patent Number: 5,843,091
[45] Date of Patent: Dec. 1, 1998

[54] EXTENSION REGULATOR FOR CATHETER CARRIED MEDICAL INSTRUMENTS

[75] Inventors: Damond C. Holsinger, Pocatello, Id.; Edward B. Madsen, Riverton, Utah

[73] Assignee: Ballard Medical Products, Draper, Utah

[21] Appl. No.: 794,162

[22] Filed: Feb. 3, 1997

Related U.S. Application Data

[63] Continuation-in-part of Ser. No. 440,562, May 12, 1995, Pat. No. 5,599,300.

[51] Int. Cl.$^6$ .................................................. A61F 11/00
[52] U.S. Cl. ............................. 606/108; 606/167; 604/48; 604/264
[58] Field of Search ..................... 604/54, 280, 52–53, 604/264, 96, 48; 606/458, 46, 108, 167

[56] References Cited

U.S. PATENT DOCUMENTS

| | | |
|---|---|---|
| 1,978,495 | 10/1934 | Landau . |
| 2,487,502 | 11/1949 | Willinsky . |
| 2,532,043 | 11/1950 | Wallace . |
| 2,545,865 | 3/1951 | Wallace . |
| 3,704,711 | 12/1972 | Park . |
| 4,444,184 | 4/1984 | Oretorp . |
| 4,473,076 | 9/1984 | Williams et al. . |
| 4,499,898 | 2/1985 | Knepshield et al. . |
| 4,516,575 | 5/1985 | Gerhard et al. . |
| 4,569,133 | 2/1986 | Schmidt . |
| 4,630,378 | 12/1986 | Kulp et al. . |
| 4,759,363 | 7/1988 | Jensen . |
| 5,035,696 | 7/1991 | Rydell . |
| 5,071,412 | 12/1991 | Noda ........................................ 604/268 |
| 5,133,359 | 7/1992 | Kedem . |
| 5,139,508 | 8/1992 | Kantrowitz et al. . |
| 5,152,772 | 10/1992 | Sewell, Jr. . |
| 5,201,732 | 4/1993 | Parins et al. . |
| 5,201,740 | 4/1993 | Nakao et al. ............................ 606/113 |
| 5,241,970 | 9/1993 | Johlin, Jr. et al. . |
| 5,250,065 | 10/1993 | Clement et al. . |
| 5,342,371 | 8/1994 | Welter et al. ............................ 606/113 |
| 5,389,100 | 2/1995 | Bacich et al. . |
| 5,431,673 | 7/1995 | Summers et al. . |
| 5,454,828 | 10/1995 | Schraga . |
| 5,478,348 | 12/1995 | Bajada . |
| 5,533,988 | 7/1996 | Dickerson et al. . |
| 5,759,186 | 6/1998 | Bachmann et al. ...................... 606/108 |

*Primary Examiner*—Ronald Stright
*Assistant Examiner*—Cris L. Rodriguez
*Attorney, Agent, or Firm*—Thorpe, North, & Western, L.L.P.

[57] ABSTRACT

An extension regulator for catheter carried medical instruments which extend from the distal end of the catheter or a point adjacent thereto, includes a regulator which is disposed on a hand-held deployment mechanism used to extend and retract the medical instrument. The deployment mechanism includes a body, and a sliding member which is attached to the connector and which slides along the body between a first position, wherein the medical instrument is retracted, and a second position wherein the medical instrument is fully extended. The regulator limits movement of the sliding member toward the second position to thereby limit extension of the medical instrument from the catheter.

48 Claims, 15 Drawing Sheets

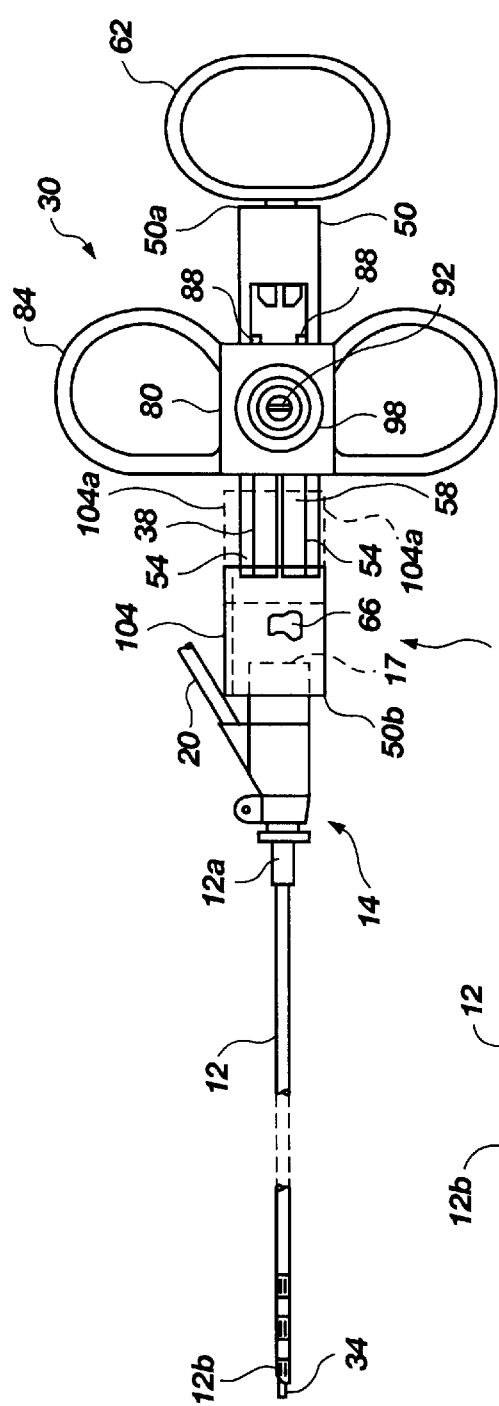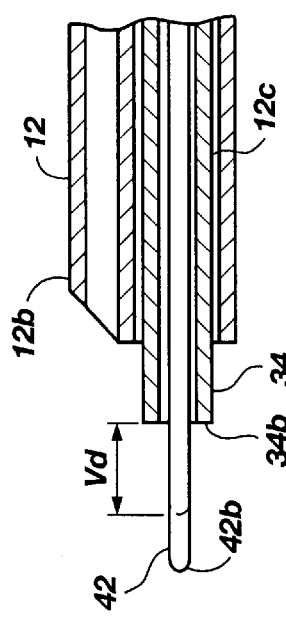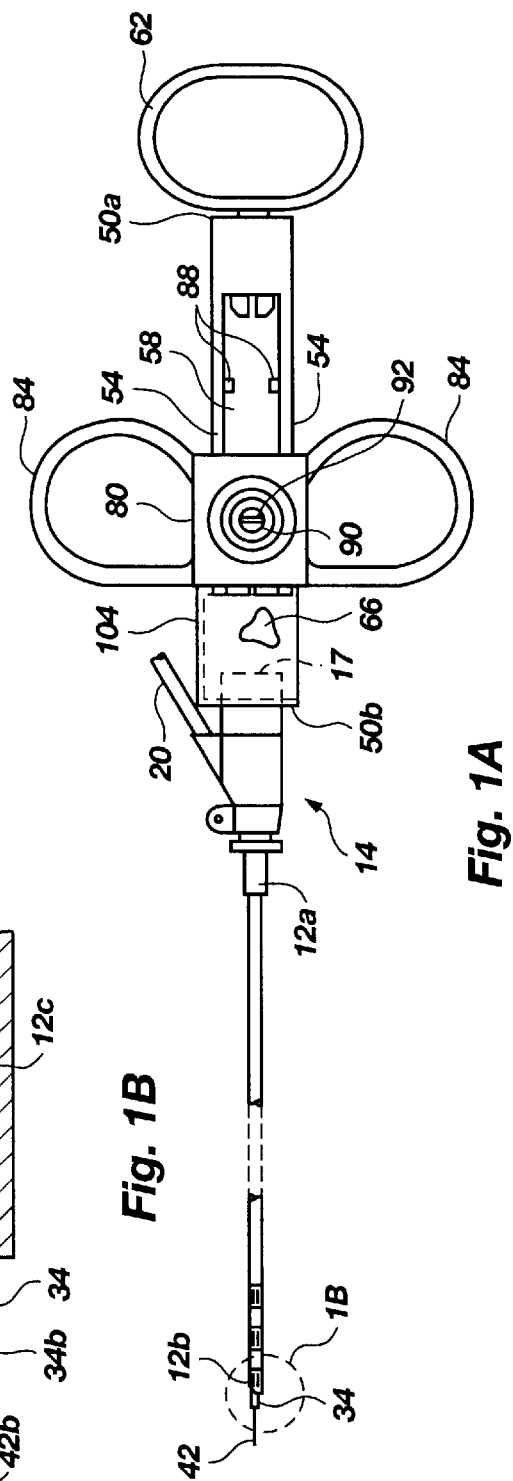

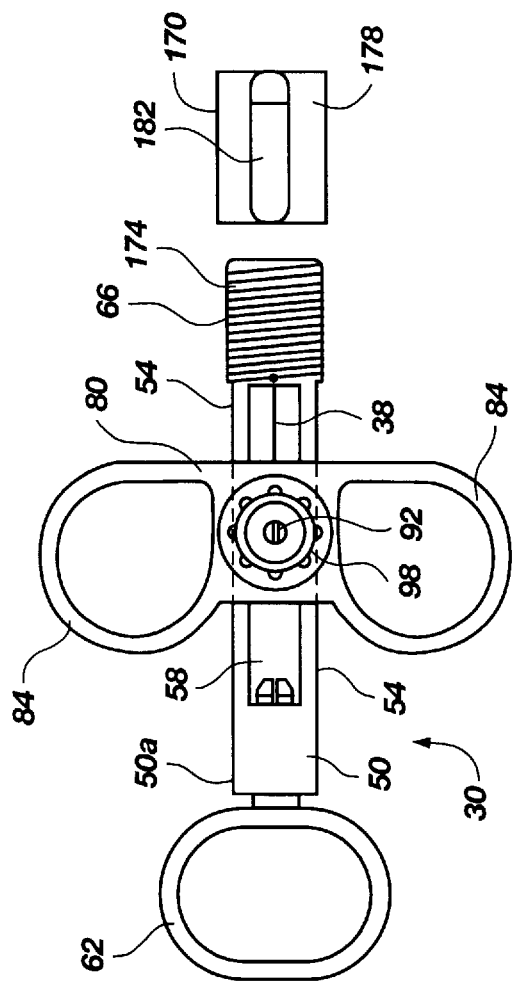

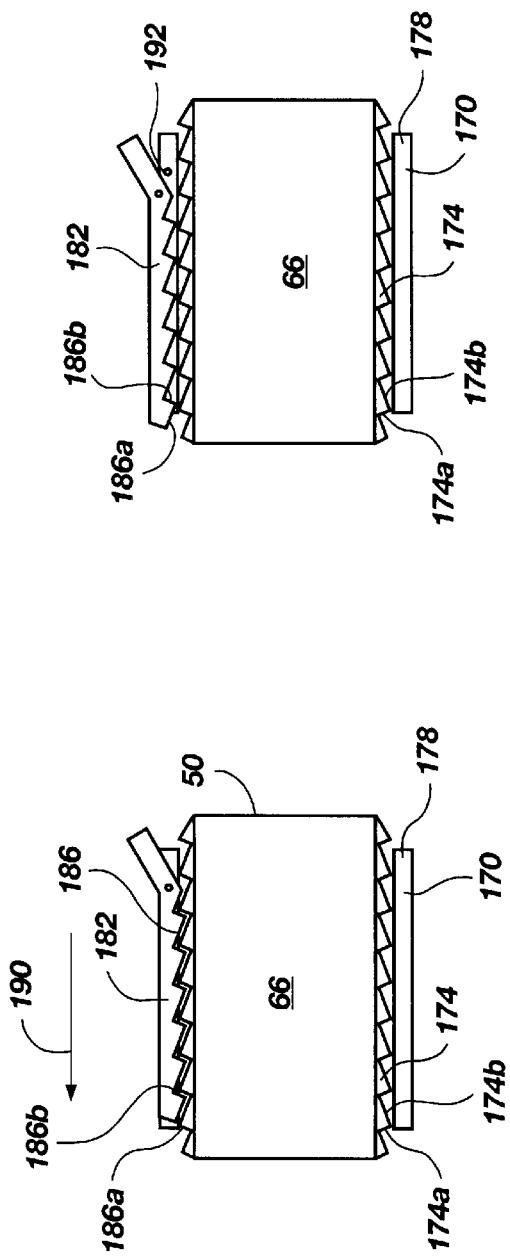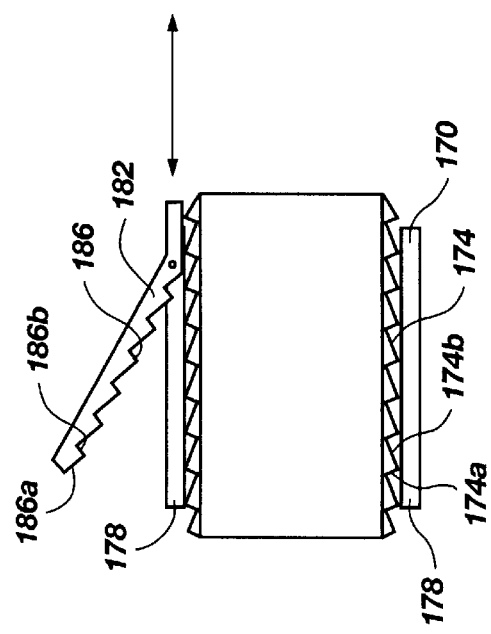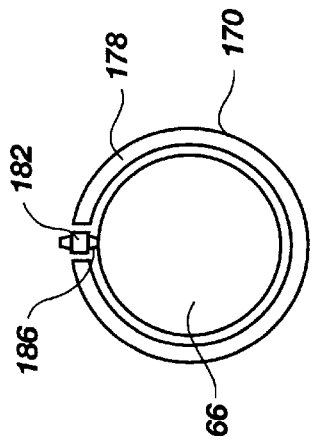

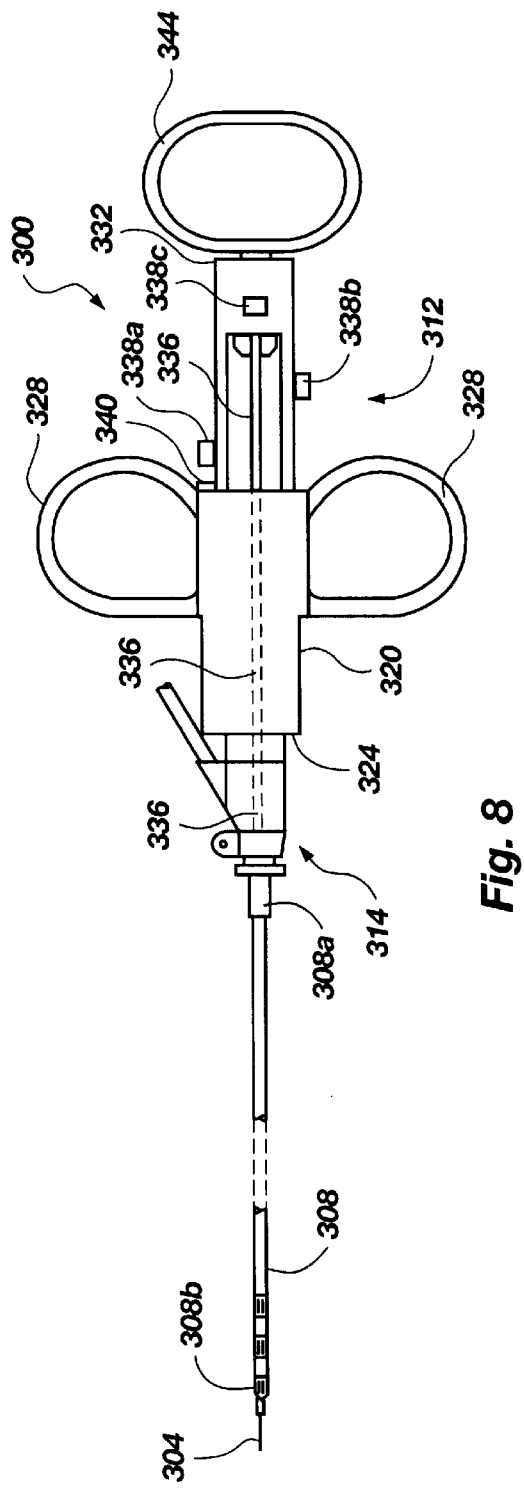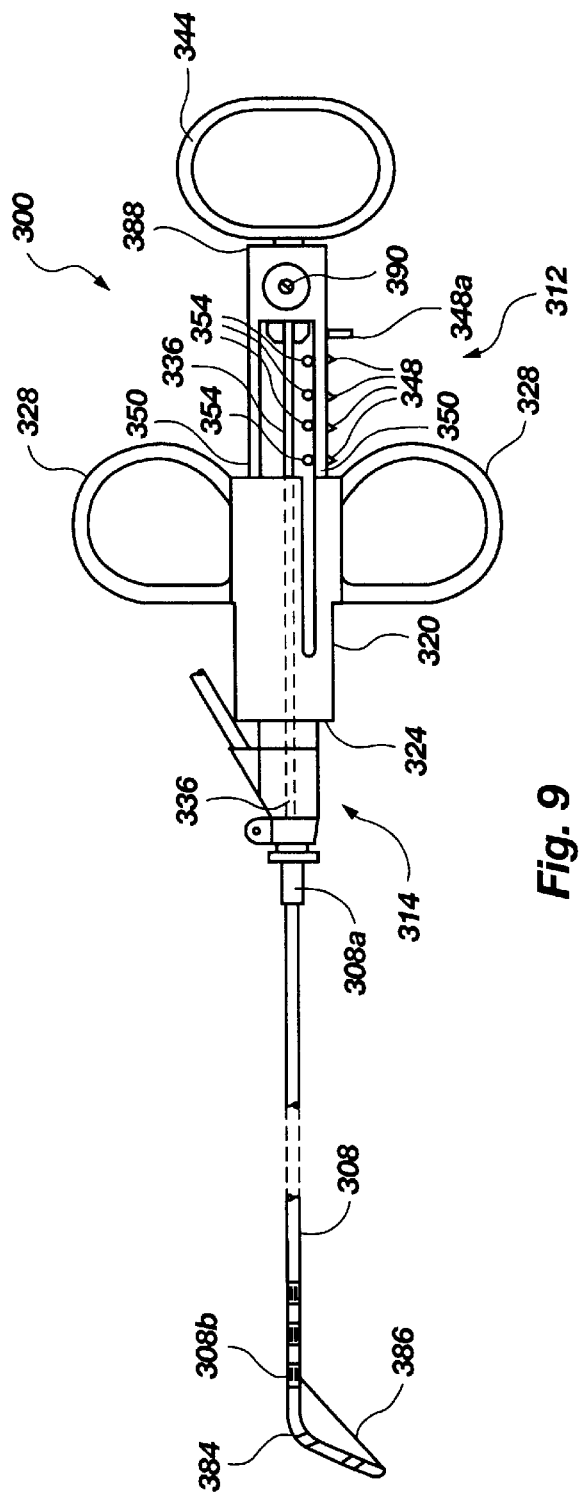

EXTENSION REGULATOR FOR CATHETER CARRIED MEDICAL INSTRUMENTS

RELATED APPLICATIONS

The present application is a continuation-in-part to U.S. patent application Ser. No. 08/440,562, filed May 12, 1995, now U.S. Pat. No. 5,599,300.

BACKGROUND OF THE INVENTION

1. Field of the Invention

The present invention relates to the control of medical instruments disposed in catheters which are used for passage through the accessory channel of an endoscope, or similar device, and into a duct within the body. More particularly, the present invention involves an apparatus and method whereby medical instruments disposed within a catheter are provided with improved extension and retraction control to prevent injury to the ducts of the patient.

2. State of the Art

Numerous procedures have evolved in the last ten years in which a catheter with a medical instrument disposed therein is inserted into a duct in the body of the patient. The catheter is advanced until it is disposed in a desire position for carrying out some task. Prior to the use of the catheterization techniques, invasive surgery was often required to perform the medical procedure.

One area which has undergone significant strides is the use of catheters in the gastrointestinal track. A number of procedures have evolved in recent years using instruments which are inserted through an endoscope in various positions in the gastrointestinal system for the purpose of diagnosis and therapeutic procedures, including insertion of stents, devices for the extraction of stones from the biliary duct, the removal of polyps and the extraction of biopsy samples.

One diagnostic technique which has come into use is Endoscopic Retrograde Cholangiopancreatography, commonly referred to as ERCP. The ERCP technique involves the placement of a side-viewing instrument, i.e. an endoscope, within the descending duodenum. A catheter is then threaded though the endoscope, and the Papilla of Vater and common bile duct are cannulated. Contrast media is then injected through the catheter so that the pancreatic ducts and the hepatobiliary tree may be visualized radiographically. In the alternative, a duodeno fiberscope can be inserted through the catheter to enable more direct visualization. Utilizing these techniques, a skilled medical practitioner can visualize approximately 90 to 95 percent of the biliary and pancreatic ducts.

While the catheter cannulation is highly desirable for avoiding unnecessary surgery and for reducing the costs of many procedures, there are still drawbacks to the technique. One major drawback is presented by the sphincter muscle which guards the entrance to the biliary tree. While the skilled practitioner is often able to slide the catheter through the sphincter muscle, it is not uncommon for the sphincter muscle to be sufficiently closed to prevent further cannulation of the biliary tree. Until relatively recently, a closed sphincter muscle required exploratory surgery to gain the desired access.

With the advancement of catheter technology has come an improved mechanism for gaining access to the biliary tree. A catheter is provided with a small electro-surgical element which enables the skilled physician to selectively incise tissue and thereby gain access to the biliary tree for further cannulization and visualization. In one common embodiment, the electro-surgical element extends out of the side of the catheter adjacent a distal tip. By using a hand-held deployment mechanism, the electro-surgical element is partially withdrawn from the catheter, thereby pulling on the distal tip of the catheter to form a bow-like shape at the distal end of the catheter. Such an embodiment is commonly referred to as a bow-knife.

In another now common embodiment, the electro-surgical element is slidably disposed within the catheter. By actuating a hand-held deployment mechanism, the electro-surgical element is extended from the end of the catheter to incise tissue, and then is retracted back into the catheter. This embodiment is commonly referred to as a needle-knife. Because of the various positions into which the catheter may be bent, the electro-surgical is generally significantly longer than the sheath of the catheter. By significantly is meant anywhere from 6 to 10 millimeters. While such a small distance does not seem significant for many applications, it is extremely significant for application of the electro-surgical element. If the element is over extended and electricity is applied to incise tissue, the patient will often require emergency surgery.

Thus, medical personnel are extremely cautious in using the needle-knife. Typically, the physician will control the endoscope (or some other visualization device) and the position of the catheter. As cuts are made in the sphincter muscle, the physician slowly advances the catheter until cannulation of the sphincter muscle has occurred.

The most significant drawback of the present situation is that the physician usually is not in control of the needle-knife. Thus, as the physician watches the progress of the cannulation, he or she tells a nurse or other medical professional when to actuate the hand-held deployment device. However, because the position of the catheter controls the amount of the electro-surgical element which extends beyond the end of the catheter, the physician is forced to tell the medical professional actuating the deployment of the electro-surgical element when the desired amount of electro-surgical element is exposed. With each advance of the catheter, the physician requests the individual operating the deployment device to extend the electro-surgical element about the same as the last time, a little more than the last time, or a little less than the last time. The individual operating the deployment device, however, is left to guess the proper positioning of the deployment device.

In U.S. Pat. No. 5,599,300, there is taught a stop which can be disposed on the hand-held deployment device to indicate where to stop advancement of the deployment device to repeat a desired amount of extension for the electro-surgical element. While the stop has been found to be of some use for indicating the desired stopping position, it often moves when repeatedly contacted during the deployment procedure. Thus, with each deployment, the electro-surgical element extends a little further beyond the end of the catheter.

Another problem with the stop has been that, despite its name, it does not provide a sure stop. If the user of the hand-held deployment device accidentally advances the electro-surgical element with even a moderately small force, the resistance supplied by the stop is overcome and the full length of the electro-surgical element can extend from the catheter. Such an accident can have serious repercussions because the electro-surgical device can easily penetrate the walls of the duct if misdirected at the time of deployment. Once the duct wall has been penetrated, the catheter procedure must usually be terminated and the patient prepared for emergency surgery.

Because of the difficulties in using a needle-knife catheter, many physicians have avoided such procedures and continue to follow less complicated, but more invasive methods. Thus, there are currently a limited number of physicians who are able to obtain the benefit of the technological advances.

In addition to needle-knife and bow knife electro-surgical catheters, there are also numerous other catheter applications in which improved control over deployment of a medical instrument from the catheter sheath is desired. Thus, there is a need for an apparatus and method which improves control over medical instrument deployment from a catheter, thereby improving safety.

SUMMARY OF THE INVENTION

Thus, it is an object of the present invention to provide an improved extension regulator for catheter carried medical instruments.

It is another object of the present invention to provide such an extension regulator which enables repeat deployments of the medical instrument at approximately the same distance from a distal end of the catheter in which the medical instrument is housed.

It is yet another object of the present invention to provide such an extension regulator which is configured with a holding position wherein the medical instrument is retained within the catheter as the catheter is advanced or retracted to thereby prevent accidental damage to the duct in which the catheter is disposed.

It is still another object of the present invention to provide an extension regulator which is adjustable while the medical instrument is deployed to thereby enable setting of the distance to which the medical instrument will extend from the catheter while the medical instrument is deployed.

It is still yet another object of the present invention to provide such an extension regulator on catheter carried instruments such as injection needles, snares, biopsy cutters and the like.

The above and other objects of the invention are realized in specific illustrated embodiments of an extension regulator for catheter carried medical instruments, wherein a catheter is used having a distal end which a medical instrument disposed therein, and a proximal end having a hand-held deployment mechanism attached thereto. The hand-held deployment mechanism is connected to the medical instrument by an elongate connector extending through the catheter. The deployment mechanism includes a body, and a sliding member which is attached to the connector and which slides along the body between a first position, wherein the medical instrument is substantially retracted into the catheter, and a second position wherein the medical instrument is fully extended out of the distal end of the catheter or an opening adjacent thereto. An extension regulator is disposed on the deployment mechanism to limit the movement of the sliding member to a range of motion between the first position and a third position which is between the first and second positions. By limiting sliding of the sliding member to the third position, the distance which the medical instrument can extend from the catheter is limited. By securing the extension regulator in place, the medical instrument will continually extend from the distal end of the catheter no more than a desired distance so long as the positioning of the catheter remains unchanged.

In accordance with one aspect of the invention, the extension regulator includes a positioning mechanism to enable multiple stepped increments in the distance which the medical instrument can extend from the catheter. The physician controlling the advancement of the catheter can then give the medical professional controlling actuation of the medical instrument a more precise indication of how much the position of the medical instrument should be changed. Thus, the physician can indicate that the medical instrument should be advanced two steps or retracted one step until the desired deployment is obtained.

In an alternative embodiment, the positioning mechanism can be provided with a continuously variable adjustment mechanism for finely tuning the exact distance the medical instrument will extend from the distal end of the catheter. To enable exact control of the extension distance of the medical instrument, the physician can have another medical professional hold the catheter in a set position while the medical instrument is deployed. The physician can then adjust the extension regulator to adjust the amount of extension of the medical instrument to achieve a desired extension. The extension regulator is then set and the physician is able to advance the catheter with a better assurance as to the amount of extension caused by each movement of the sliding member.

In accordance with another aspect of the present invention, the extension regulator includes a full retract position in which the extension regulator maintains the sliding member in the first position, thereby maintaining the medical instrument within the catheter. Maintaining the medical instrument within the catheter prevents it from accidentally extending from the catheter and damaging the duct when the catheter is being advanced or retracted in the duct. Thus, even if the medical professional holding the hand-held deployment device were to accidentally attempt to move the slide member, the medical instrument would not advance from the catheter.

In use, the extension regulator will typically be disposed on the body of the hand-held deployment device forward of the sliding member. An engagement mechanism is provided between the extension regulator and the body to selectively prevent the extension regulator from sliding along the body. Once the extension regulator is moved into a desired position, the range of motion of the sliding member is curtailed, thereby limiting the amount of extension of the medical instrument.

The advantages which are obtainable by use of the present invention provide a significant advance over the prior art. No longer is the medical professional using the hand-held deployment device left to guess the proper position of the sliding member to achieve the desired extension of the medical instrument. With respect to cannulation of the sphincter muscle of the biliary tree, the physician is able to more efficiently advance the catheter, as he or she knows the extent to which the medical instrument will extend from the catheter. Not only will such improve efficiency, it will also decrease the amount of emergency surgeries which are caused by improperly incising tissue of the biliary tree, or of other ducts within the body.

In addition to its applicability to needle-knifes, the present invention can be used effectively with other catheter carried instruments such as injection needles, biopsy devices, snares, and the like. Thus, the present invention provides a solution to a wide array of problems which currently accompany the use of medical instruments which are carried by and deployed from catheters.

BRIEF DESCRIPTION OF THE DRAWINGS

The above and other objects, features and advantages of the invention will become apparent from a consideration of the following detailed description presented in connection with the accompanying drawings in which:

FIG. 1 is a top plan view of a needle-knife assembly where the needle-knife sheath, connecting tube and the needle-knife are disposed within a multi-lumen catheter with the needle-knife retracted in a sheathed position;

FIG. 1A is a top plan view of the embodiment of needle-knife assembly shown in FIG. 1, wherein the needle-knife is in a deployed position so that it extends from the distal end of the catheter and needle-knife sheath;

FIG. 1B is a side cross-sectional detail view of the distal end of the catheter, catheter sheath and the needle-knife in the deployed position;

FIG. 7 is a top exploded view of an alternate embodiment of the present invention wherein the extension regulator is threadedly engaged to the body of the needle-knife actuator assembly;

FIG. 7A is a cross-sectional view of the extension regulator of FIG. 7 being disposed about the end portion of the body of the deployment mechanism;

FIG. 7B is a cross-sectional view of the extension regulator of FIG. 7 being disposed about the end portion of the body of the deployment mechanism and being moved in a ratchetting process;

FIG. 7C is a cross-sectional view of the extension regulator of FIG. 7 being disposed about the end portion of the body of the deployment mechanism and being slidably moved along the end portion;

FIG. 7D is an end view of the extension regulator of FIGS. 7 through 7C and the end portion of the deployment mechanism;

FIG. 8 is a top plan view of yet another alternate embodiment of the present invention for use when the sliding member is moved in a plunger-like manner; and FIG. 9 is a top plan view of an alternate embodiment of the present invention for use with sliding members which move in a plunger-like manner.

DETAILED DESCRIPTION

Figure 1C:
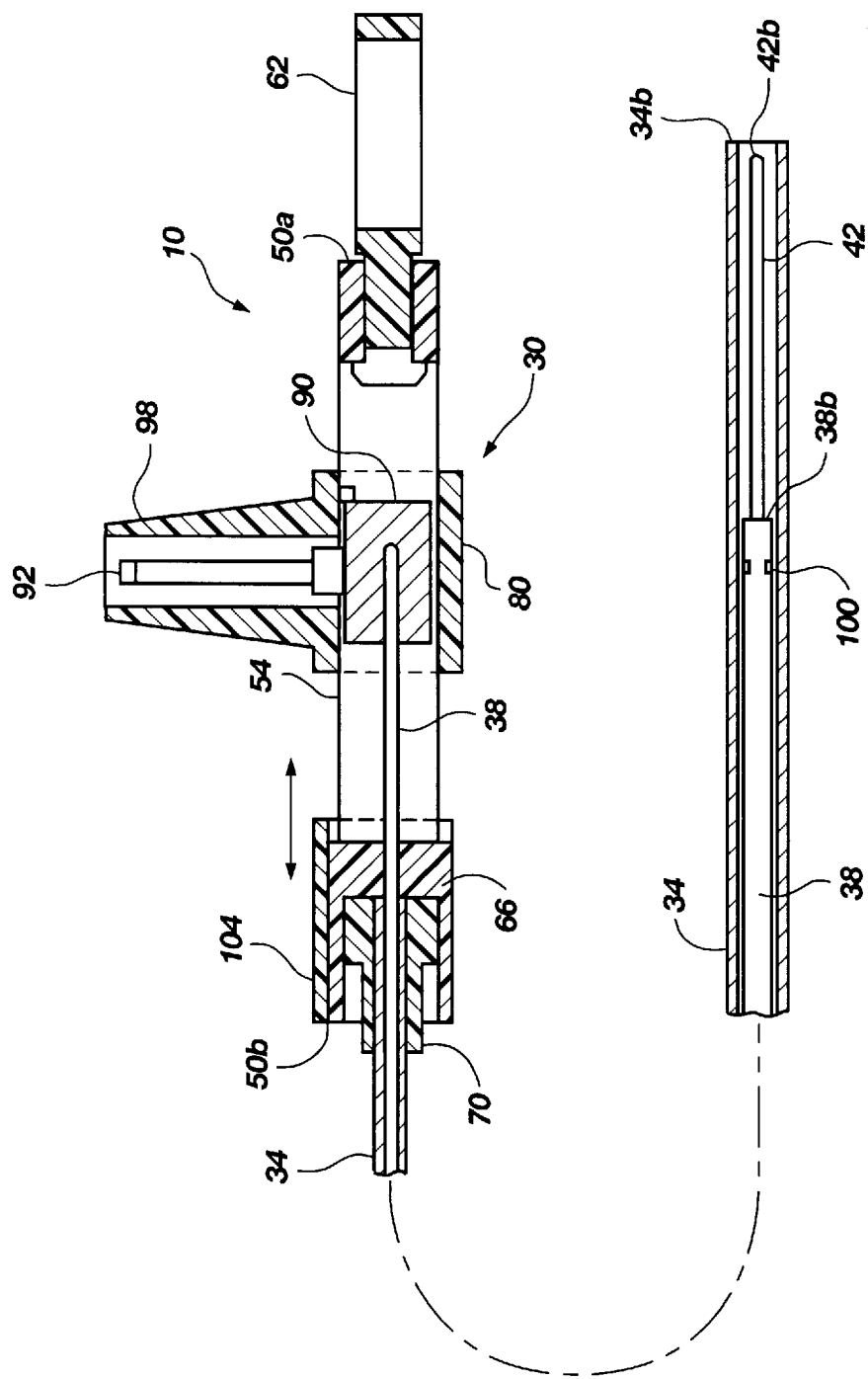
FIG. 1C is a side cross-sectional view depicting details of the deployment mechanism of the needle-knife actuator assembly, the sheath and the connecting tube.

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Referring to FIG. 1, there is shown a top plan view of a needle-knife assembly, generally indicated at 10, which is adapted for use with a multi-lumen catheter 12. The multi-lumen catheter 12 has a connector 14 attached to a proximal end 12a thereof, the connector including a luer lock hub 17 for attachment of the needle-knife assembly. Also present is a polymeric tube 20 which may be used for injection of a contrast medium or some other purpose.

The needle-knife assembly 10 is principally comprised of a deployment mechanism 30 and an elongated sheath 34 having an elongated connecting tube 38 and needle-knife 42 (FIG. 1B) disposed therein. The deployment mechanism 30 includes a body 50 having a pair of rails 54 which are configured to define a centrally disposed slot 58. Body 50 includes a first, proximal end 50a to which a thumb ring 62 is attached, and a second, distal end 50b having an end portion 66 at which a fitting 70 (FIG. 1C) is located for receiving the sheath 34 and connecting tube 38 as described below. A sliding member 80 is slidably connected to the body 50. The sliding member 80 preferably includes a pair of opposed finger rings 84 which enable a user to grasp the same between two fingers—typically the forefinger and index finger. By placing a thumb through thumb ring 62, the sliding member 80 may be advanced towards the second end 50b of the body 50. As the sliding member 80 moves, it pushes the connecting tube 38 forward and thereby deploys the needle-knife 42. The sliding member 80 may also be freely moved away from the second end 50b of the body 50 until the sliding member contacts a pair of stops 88. When the sliding member 80 is disposed sufficiently toward the first end 50a of the body to contact the stops 88, the connecting tube 38 is moved a sufficient distance to withdraw the needle-knife 42 into the sheath 34 as described below.

The sliding member 80 has an internally disposed brass insert 90 (FIG. 1A) which electrically communicates with a brass binding post 92. The brass insert 90 and the brass binding post 92 form an electrical connection for coupling a power source (not shown) to the needle-knife 42. The power source provides a cutting/coagulating current with which the needle-knife incises tissue. The binding post 92 is situated within a connector cap 98 integral with the sliding member 80.

As shown in FIG. 1C, the elongated connecting tube 38 is attached to and electrically communicates with the insert 90. The connecting tube 38 is fabricated from a conductive material, such as stainless steel, and extends through the fitting 70 in the second end 50b of the body 50 and terminates in a distal end 38b. The connecting tube 38 has a hollow bore (not shown) into which the needle-knife 42 is partially disposed near the distal end 38b. The connecting tube 38 is crimped over or otherwise attached to the needle-knife 42 at location 100 adjacent the distal end 38b of the connecting tube and in such a manner as to avoid interference with conduction of current through the connecting tube and needle knife. The fitting 70 tightly receives the elongated tubular sheath 34 and provides strain relief. In a preferred embodiment, the sheath 34 is made from polyimide material with a Teflon coating. This combination of materials enables fabrication of a sheath 34 with an outer diameter as small as approximately 0.035 inches, to enable advancing the same through one lumen of the multi-lumen catheter 12 used in an ERCP procedure in accordance with the present invention. The use of polyimide material provides good kink resistance, even if the sheath is fabricated with a very thin wall thickness, and the Teflon coating provides a smooth surface to enable the sheath 34 to be easily inserted and removed from the catheter 12.

FIG. 1B shows the orientation of the sheath 34 disposed within the catheter 12, where the distal end 34b of the sheath extends a nominal distance from the distal end 12b of the catheter 12. The needle-knife 42 extends from the distal end 34b of the sheath 34 so that a distal end 42b of the needle-knife is available to incise tissue with the cutting/coagulating current when desired.

In the preferred embodiment, the needle-knife 42 has a diameter of approximately 0.006 inches, and is fabricated from a "memory" metal alloy such a Nitonil. As is known in the art, memory metals undergo a crystalline phase change and thermoelastically deform when heated and cooled. These crystal phase changes between what are known as high temperature Austenite and low temperature Martensite, enable a component made from such material to contract when heated, and to return to its original configuration when cooled. Moreover, the stress-strain behavior of a memory metal alloy makes the material much easier to deform when cooled (martensite) than when at an elevated temperature (austenite). In the present invention, the use of this material is susceptible to deformation during the cutting procedure. The memory material helps it return to its original orientation if deformed by stress during the cutting procedure. When the needle-knife 42 is heated by applying the cutting/coagulating current, the crystalline transformation to Austenite makes it much more difficult to deform. If a sufficient force is then applied to the needle-knife 42 during the procedure, the material can strain to relieve the applied stress as it transforms back to Martensite. Once the stress is reduced, it will unstrain and revert back to Austenite. Finally, after the applied current is removed, the resulting cooling of the needle-knife material and associated crystal phase change to Martensite makes it more flexible.

Referring now more specifically to FIGS. 1, 1A and 1B, the needle-knife 42 is normally disposed so as to remain in a sheathed position within sheath 34 with respect to the distal end 34b thereof. The sheath 34 is inserted through lumen 12c of catheter 12 so that the sheath extends to a position at or slightly distal from the distal end 12b of the catheter 12. The catheter assembly is attached to the deployment mechanism 30 by threading the luer lock hub 17 (as shown in FIG. 1) of the connector 14 into the fitting 70 at the second, distal end 50b of the body 50.

Figure 4:
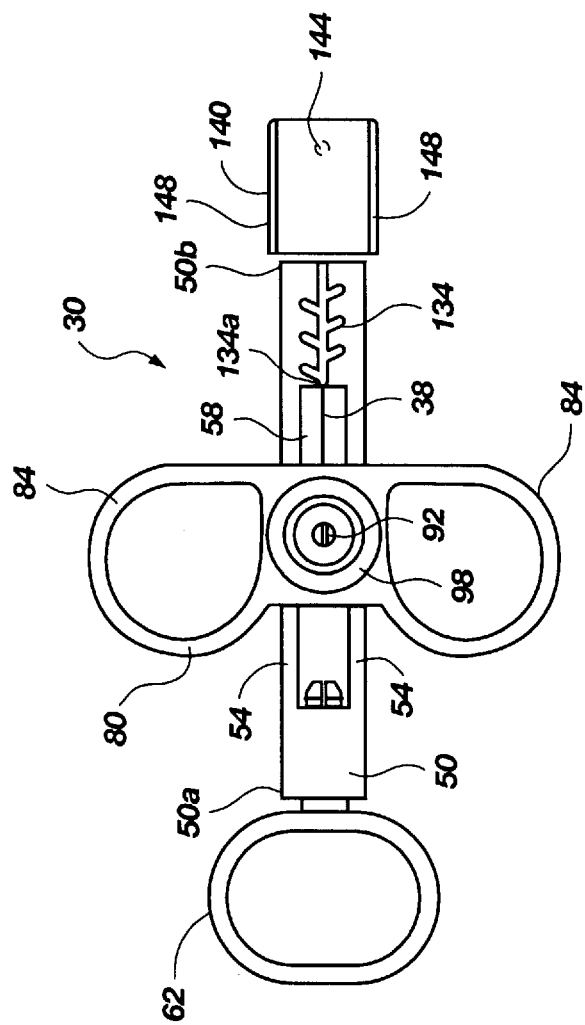
FIG. 4 is a top, exploded view of a needle-knife actuator assembly having a modified configuration of the embodiment shown in FIGS. 3 through 3C.

Preferably, the needle-knife assembly 10 is pre-loaded in the catheter 12. This facilitates the use of the needle-knife assembly in a typical ERCP procedure using a multi-lumen catheter. In this method, the physician advances the catheter 12 through an endoscope (as shown in FIG. 4) and into the patient's duodenum proximal to the entrance to the common bile duct, typically into or just above the papillary orifice. By grasping the deployment mechanism 30 by finger rings 84 and thumb ring 62, the physician then advances the sliding member 80 towards the second end 50b of the body 50 to cause the needle-knife 42 to extend from the distal end 34b of the sheath 34 as shown in FIGS. 1A and 1B.

The physician applies an appropriate amount of cutting/coagulating current to the needle-knife 42 through the binding post 92, and manipulates the needle-knife by using the elevator and/or positioning controls of the endoscope to incise tissue. Typically, a 3–5 millimeter across by 2–4 millimeter deep incision into the papilla is sufficient. The needle-knife 42 is then retracted into the distal end 34b of the sheath 34 by moving the sliding member 80 rearwardly towards the first end 50a and against the stops 88 of the deployment mechanism 30. This enables the physician to insert the catheter 12 into the common bile duct with less effort. Once access is gained to the common bile duct, the physician can then cannulate and visualize the same in accordance with the ERCP procedure described in the foregoing. The sheath 34 and needle-knife 42 can be left within the first lumen 12c of the catheter 12 to function as a stiffening element to enable advancing the catheter into the common bile duct, or the sheath 34 and needle-knife 42 may be withdrawn from the catheter 12, and a wire guide then inserted in its place by simply unthreading the luer lock hub 17 from deployment mechanism 30 and attaching a wire guide feeding apparatus in a manner known in the art. The common bile duct can then be visualized by infusing a contrast medium through the multi-lumen catheter 12. To facilitate further cannulation and/or visualization of the common bile duct, the wire guide may be advanced along the duct and the catheter 12 then repositioned by advancing the catheter over the wire guide to the appropriate location, and the infusion procedure may be repeated.

As was mentioned in the background section, however, the process of incising the tissue of the sphincter muscle requires precise control of the needle-knife 12. The physician, however, holds the endoscope (not shown) and the catheter 12, and is therefore not able to perform the actuation of the needle-knife 42. The physician must thus instruct the nurse or other medical professional as to the desired extension of the needle-knife 42 while observing the sphincter muscle through the endoscope. As the physician advances the catheter, the nurse must attempt to repeat the degree of extension at each desired cut location. Such can be extremely difficult and the repeated fine movements of the deployment mechanism 30 can tire the hand of the operator.

To assist with these concerns, U.S. Pat. No. 5,599,300 (the entirety of which is expressly incorporated herein) discloses a slidable stop, substantially the same as slidable stop 104, which is formed by a cylindrical housing disposed on the body 50 adjacent the distal end 50b. The slidable stop 104 was added to enable the user to customize the range of motion in which the sliding member 80 is moved. Rather than sliding between a first proximal position and a second distal position, the range of motion of the sliding member is limited to movement between the first proximal position, and a third, desired position between the first and second positions. In other words, the sliding stop 104 enables the user to select a desired extension distance $V_d$ relative to the distal end 34b of the sheath 34 prior to moving the sliding member 80 towards the second end 50b of the body 50. Thus, for example, when a physician tells the nurse operating the deployment device 30 that the desired extension has been obtained, the slidable stop 104 is slid along the body 50 until it contacts the sliding member 80, as indicated at 104a (FIG. 1). When the sliding member 80 is slid back toward the proximal end 50a of the body, the slidable stop 104a remains in place, indicating the desired forward position of the sliding member. The next time the user is to advance the sliding member 80, the desired (third) location for stopping the sliding member is indicated by the slidable stop 104a.

While the slidable stop 104a has provided an advantage over the customary practice of simply guessing where to stop with each advancement of the sliding member 80, several problems have remained. The slidable stop 104 is made out of a plastic which slides easily on the plastic body 50. The easy sliding of the slidable stop 104 facilitates placement so as to mark the forward desired limit of the sliding member 80. However, it also allows the slidable stop to be easily removed from the desired location. Unless the user is careful to stop the sliding member 80 before contacting the slidable stop 104, the slidable stop is nudged forward. The next time the sliding member 80 is advanced, the needle-knife 42 will extend further from the catheter than desired. If the actuation is repeated several times, the difference between actual and desired extension of the needle-knife 42 can be significant.

Another problem with the slidable stop 104 is that the the stop will not prevent accidental advancement of the needle-knife. Because the deployment mechanism is held in the user's hand, a simple twitch or other involuntary movement can cause the needle-knife 42 to be deployed to its maximum extent. Such a deployment can incise tissue in the biliary tree or adjacent structures and force emergency surgery.

Figure 2:
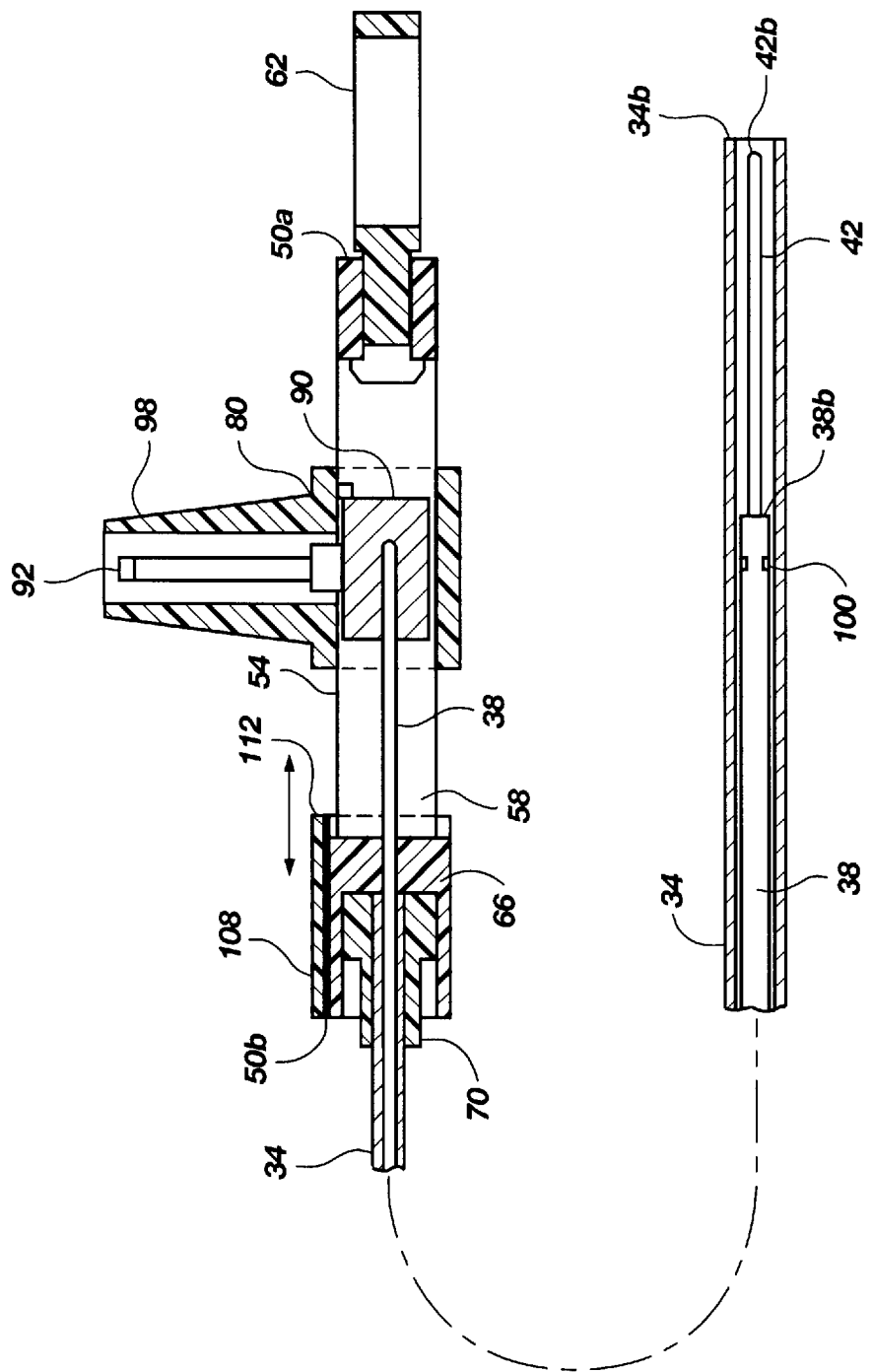
FIG. 2 is a cross-sectional view of an alternate embodiment of a slidable stop disposed on a needle-knife actuator assembly.

FIG. 2 shows a cross-sectional view of an alternate embodiment of the present invention which alleviates some of these concerns. To provide an indication of a desired position, the embodiment shown in FIG. 2 provides a slidable stop 108 which is configured in substantially the same manner as the slidable stop 104 in FIGS. 1, 1A and 1C. However, an under surface of the slidable stop is provided with a friction layer 112 in the form of a coating of material selected to frictionally engage the second end 50b of the body 50. While the friction layer 112 requires more force to move the slidable stop into the desired position when marking the stop point for the sliding member 80, the slidable stop 108 is much more difficult to displace than the slidable stop 104. To further facilitate placement of the stop 108 while preventing the stop from being easily moved by the sliding member 80, the friction layer could be contoured to provide increased resistance to movement toward the second, distal end 50b of the body 50, than toward the first, proximal end 50a.

The friction layer 112 may be formed of rubber or any of a number of elastomeric materials. The friction layer 112 may be coated on the entire inner surface of the slidable stop 108, or only on portions which remain in contact with the portion of the body 50 distal from the slot 58.

Figure 3:
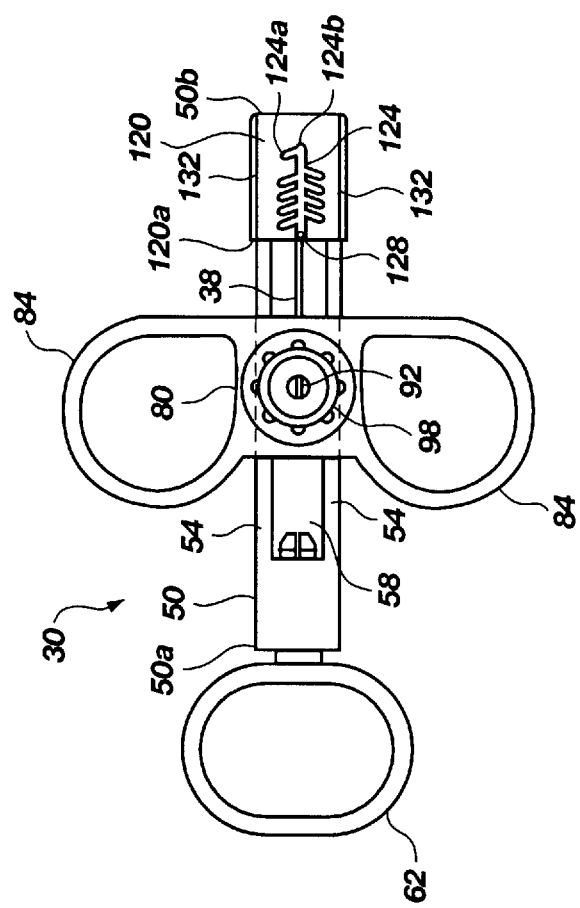
FIG. 3 is a close-up, top view of a deployment mechanism of the needle-knife actuator assembly having another embodiment of the present invention disposed thereon to affirmatively prevent forward advancement of the sliding member beyond a desired position.

Referring now to FIG. 3, there is shown a close-up, top view of the deployment mechanism 30 of a needle-knife actuator assembly as described with respect to FIGS. 1 through 1C. The deployment mechanism 30 includes an elongate body 50 having a first, proximal end 50a and a second, distal end 50b. Attached to the first, proximal end 50a is the thumb ring 62 which enables the user to maintain a sure grip on the deployment mechanism 30.

The sliding member 80, including the finger rings 84, the binding post 92 and the connecter cap 98, slide along the body 50 between a first, proximal position and a second, distal position. Disposed on the second, distal end 50b of the body 50 is an extension regulator in the form of a slidable stop 120. The slidable stop 120 has a plurality of channels 124 formed therein. The channels 120 are preferably disposed in an alternating, spaced relationship.

A post 128 is attached to or formed integrally with the body 50 on the distal end 50b adjacent the slot 58. The channels 124 are preferably sloped so that when the post 128 is disposed in one of the channels, forward movement of the slidable stop 120 is prevented. To provide improved control, the channels 124 are provided in a staggered arrangement with each slot providing a small advancement of the slidable stop toward the proximal end 50a of the body 50. As shown in FIG. 3, the slidable stop 120 includes eight staggered channels which extend from a central channel. When used with a needle-knife extension regulator configured to provide 8 millimeters of needle-knife extension, the movement of the post 128 to an adjacent channel will advance or contract the maximum extension available by about 1 millimeter (the exact amount of change is dependent on the disposition of the sheath within the patient's body).

The channels 124 also include a terminal channel 124a which is disposed a sufficient distance from the proximal end 120a of the slidable stop 120 that positioning the post 128 within the terminal channel ensures that the needle-knife is retracted into the sheath 34. The terminal channel 124a may also include a nub 124b to ensure that the post 128 is not accidentally removed from the terminal channel. By placing the post 128 in the terminal channel 124a, the physician can advance or retract the catheter having the needle-knife disposed therein without fear that the needle-knife will accidentally protrude from the catheter and damage the duct in which the catheter is disposed.

Also shown in FIG. 3 are a pair of ribs 132 which extend along the slidable stop 120. The ribs 132 are used to rotate the slidable stop 120 slightly to facilitate movement of the post 128 between the respective channels 124 and thereby adjust the extent to which the needle-knife 42 is able to extend from the sheath 34.

Figure 3A:
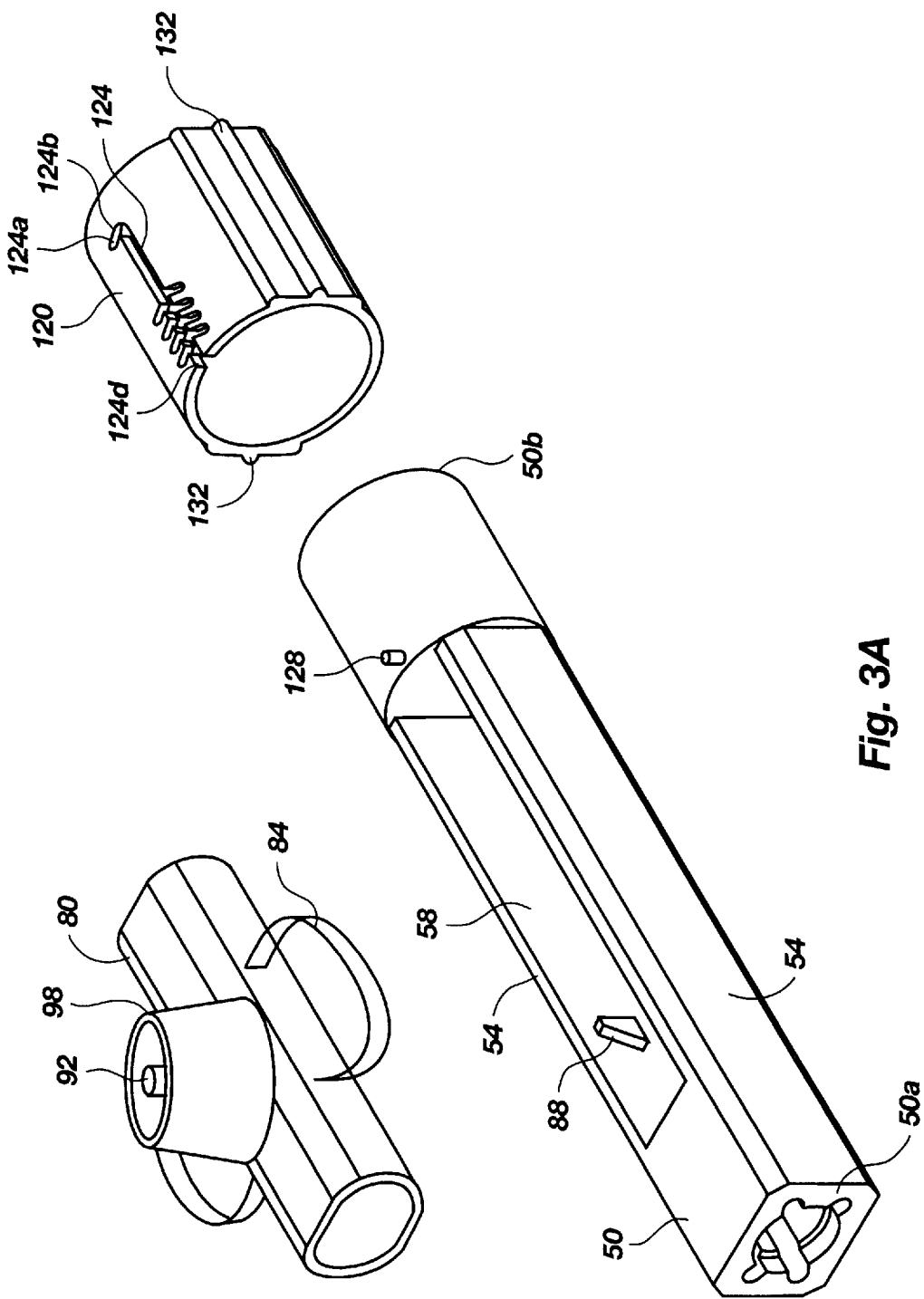
FIG. 3A is an exploded view of the body, sliding member and extension regulator of the needle-knife actuator shown in FIG. 3.

Turning now to FIG. 3A, there is shown an exploded view of the body 50, the sliding member 80 and the extension regulator in the form of a slidable stop 120. The body 50 is formed by an elongate piece of plastic having the first, proximal end 50a and the second, distal end 50b with a slot 58 defined by opposing rails 54. The sliding member 80 is slidably mounted over the body 50. Because of the post 128, the sliding member 80 is typically slid over the proximal end 50a of the body 50. Once the thumb ring (not shown in FIG. 3A) in attached to the proximal end 50a of the body 50, the sliding member 80 is locked between the thumb ring and the post 128. When the insert 90 is placed into the sliding member 80, the insert engages the stops 88 formed on the rails, and thereby limits proximal movement of the sliding member 80.

The slidable stop 120 is typically provided with an open end 124d at the base of the channels 124 to enable the slidable stop to be mounted on the body 50 by simply sliding the stop over the distal end 50b of the body while the open end is in alignment with the post 128. When the needle-knife actuation assembly is fully assembled, as shown in FIGS. 1 and 1A, the polymeric tube 20 will generally prevent the slidable stop 120 from sliding off the body. In the alternative, the channels 124 could be formed without an open end, and the slidable stop 120 could be configured to deform sufficiently to slide over the post 128 for initial placement. In light of the present disclosure, those skilled in the art will appreciate numerous other configurations for the slidable stop 120.

Figure 3B:
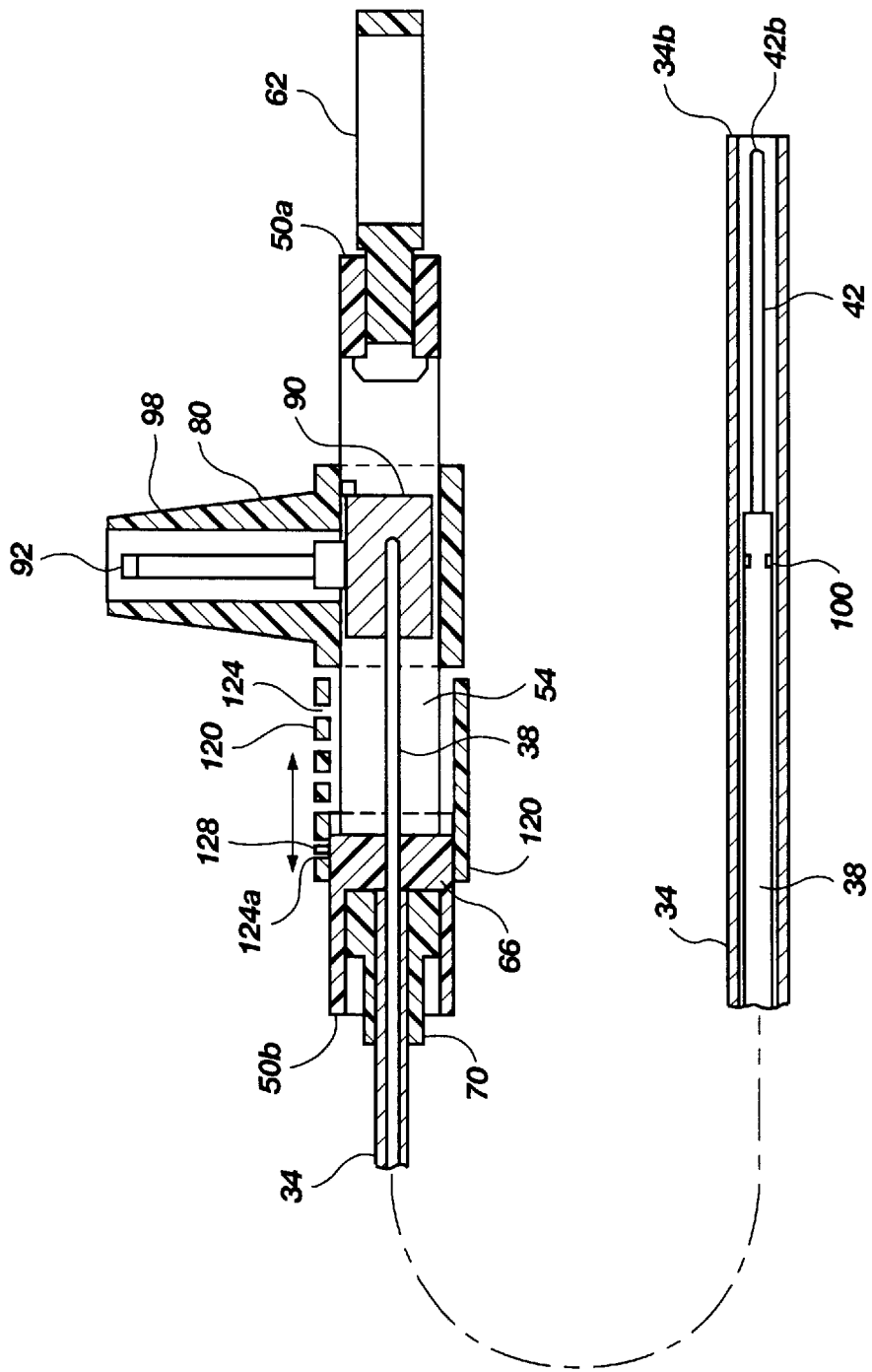
FIG. 3B is a side cross-sectional view of the embodiment of the present invention shown in FIGS. 3 and 3A, the extension regulator being disposed in a first position in which the sliding member is unable to move a sufficient distance to extend the needle-knife out of the needle-knife sheath.

FIG. 3B is a side cross-sectional view of the embodiment of the present invention shown in FIG. 3, the slidable stop 120 regulating extension of the needle-knife 42 disposed in a first position in which the sliding member 80 is unable to move a sufficient distance to extend the needle-knife out of the needle-knife sheath 34. The post 128 is nested in the terminal channel 124a, and thereby holds the slidable stop 120 adjacent its most proximal position. With the slidable stop 120 in such a position, the physician can freely move the needle-knife sheath 34 without risk of the needle-knife 42 damaging the duct in which the catheter is disposed.

While the risk of a needle-knife 42 without a current applied thereto damaging a duct is not great, the present invention is equally applicable to other devices such as injection needles, biopsy devices and other medical instruments which can cause significant damage to a duct if not properly shielded. Thus, the present invention provides a simple yet effective way to ensure safety during advancement or withdrawal of the catheter/sheath.

Figure 3C:
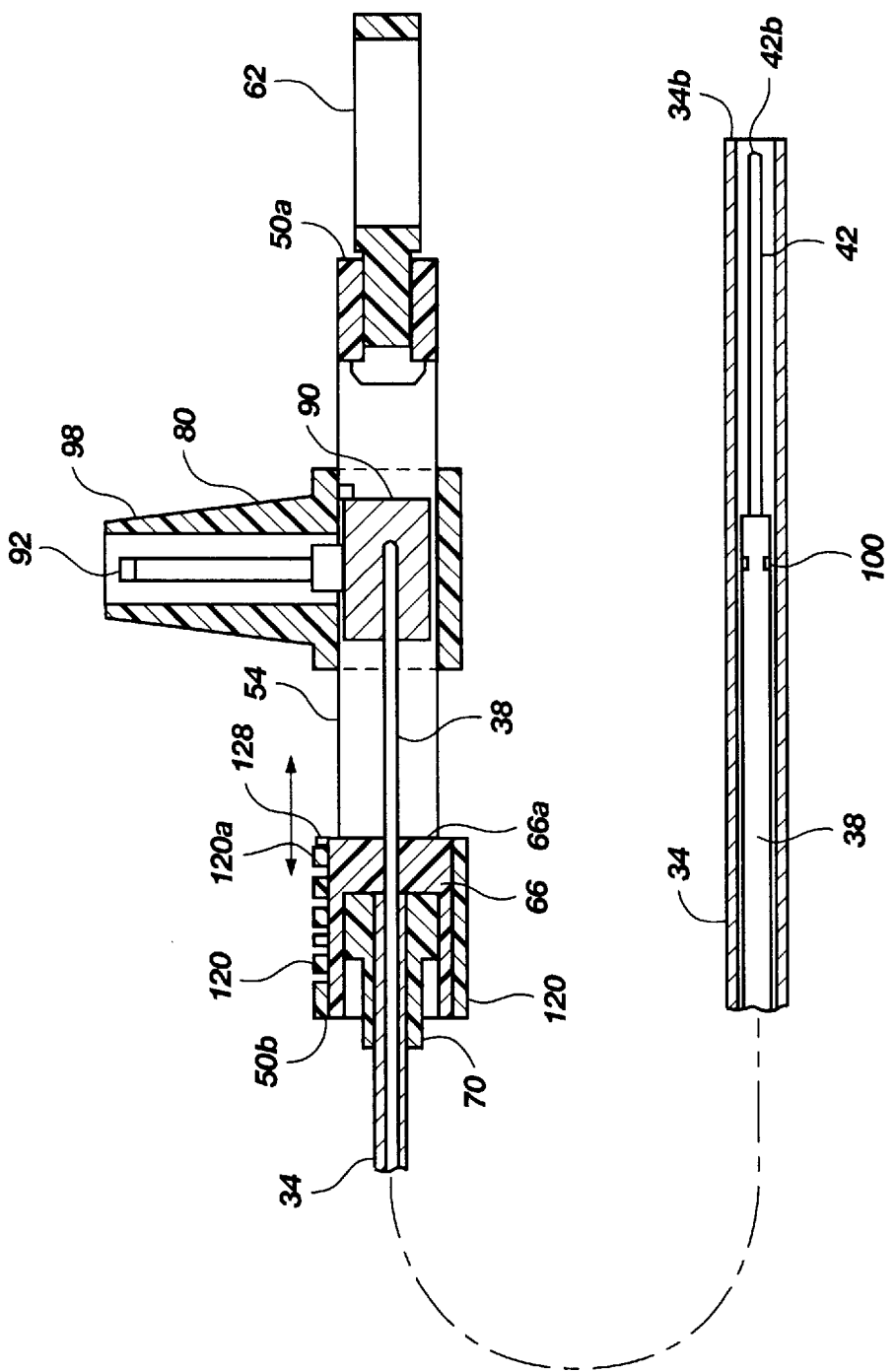
FIG. 3C is a side cross-sectional view of the embodiment of FIGS. 3 and 3A, wherein the extension regulator is disposed in a second position in which the sliding member can slide to fully extend the needle-knife.

FIG. 3C is a side cross-sectional view of the embodiment of FIG. 3, wherein the slidable stop 120 which regulates extension of the needle-knife 42 is disposed in a second, distal position in which the sliding member 80 can slide to fully extend the needle-knife 42. To facilitate such movement of the needle-knife 42, the post 128 must be disposed adjacent to the proximal end 120a of the stop 120 so that the stop does not extend beyond the proximal end 66a of the end portion 66. When disposed in such a position, the stop 120 provides no barrier to movement of the sliding member 80 into its second, distal position, thereby achieving maximum extension of the needle-knife 42.

By positioning the slidable stop 120 at a third position, between the first, extreme proximal position (FIG. 3B) and the second, extreme distal position (FIG. 3C), the user of the deployment mechanism 30 is able to more accurately determine the extent to which the needle-knife 42 will extend from the sheath 32 with each actuation. The slidable stop 120 is easy to use and provides a much safer application of the electro-surgical instrument than the prior art method of repeatedly guessing where to stop advancement of the device. Because the desired location is determined and the slidable stop 120 is locked into place, the procedure may occur more rapidly without any increased risk to the patient.

Turning now to FIG. 4, there is shown a top, exploded view of the deployment mechanism 30 of a needle-knife actuator assembly having a modified configuration of the embodiment shown in FIGS. 3 through 3C. Rather than having a post extending upwardly from the end portion 66 of the body 50, the embodiment shown in FIG. 4 has a plurality of grooves 134 formed in the end portion. A cylindrical housing forming a slidable stop 140 is provided with a downwardly extending post 144 which is configured to nest within the grooves 134. The slidable stop is preferably made of a transparent material to enable the user to see the post 144. Additionally, the post 114 could be colored to further enhance visibility.

By controlling in which of the grooves 134 the post 144 is disposed, the user can control the position of the slidable stop 140 in such a manner as to regulate the distance the sliding member 80 can slide toward the distal end 50b of the body 50. Because the reversal between the position of the post 144 and the grooves 134, the grooves will typically have the opposite orientation as when they are formed in the housing of the stop 120 (FIG. 3A).

Such control of the sliding member 80, in turn, controls the extent to which the needle-knife 42 is extendable out of the sheath 34. When the post 144 of the slidable stop 140 is disposed in the proximal most groove 134a, the slidable stop 140 is positioned in its most proximal position. In such a position, the slidable stop 140 prevents the sliding member 80 from sliding forwardly a sufficient distance to extend the needle-knife 42 from the sheath 34.

Each groove 134 distal from the proximal most groove 134a provides one step in a series of controlled extension steps. When the user deploys the needle-knife for the first time, the physician viewing the extension of the needle-knife can instruct the user to proceed to the next step until a desired extension is obtained. Typically, this will occur in 0.5 to 1 millimeter increments. Once the desired position is obtained, the user is able to simply actuate the deployment mechanism 30 to extend the needle-knife without guess work and without concern of accidental overextension.

Figure 4A:
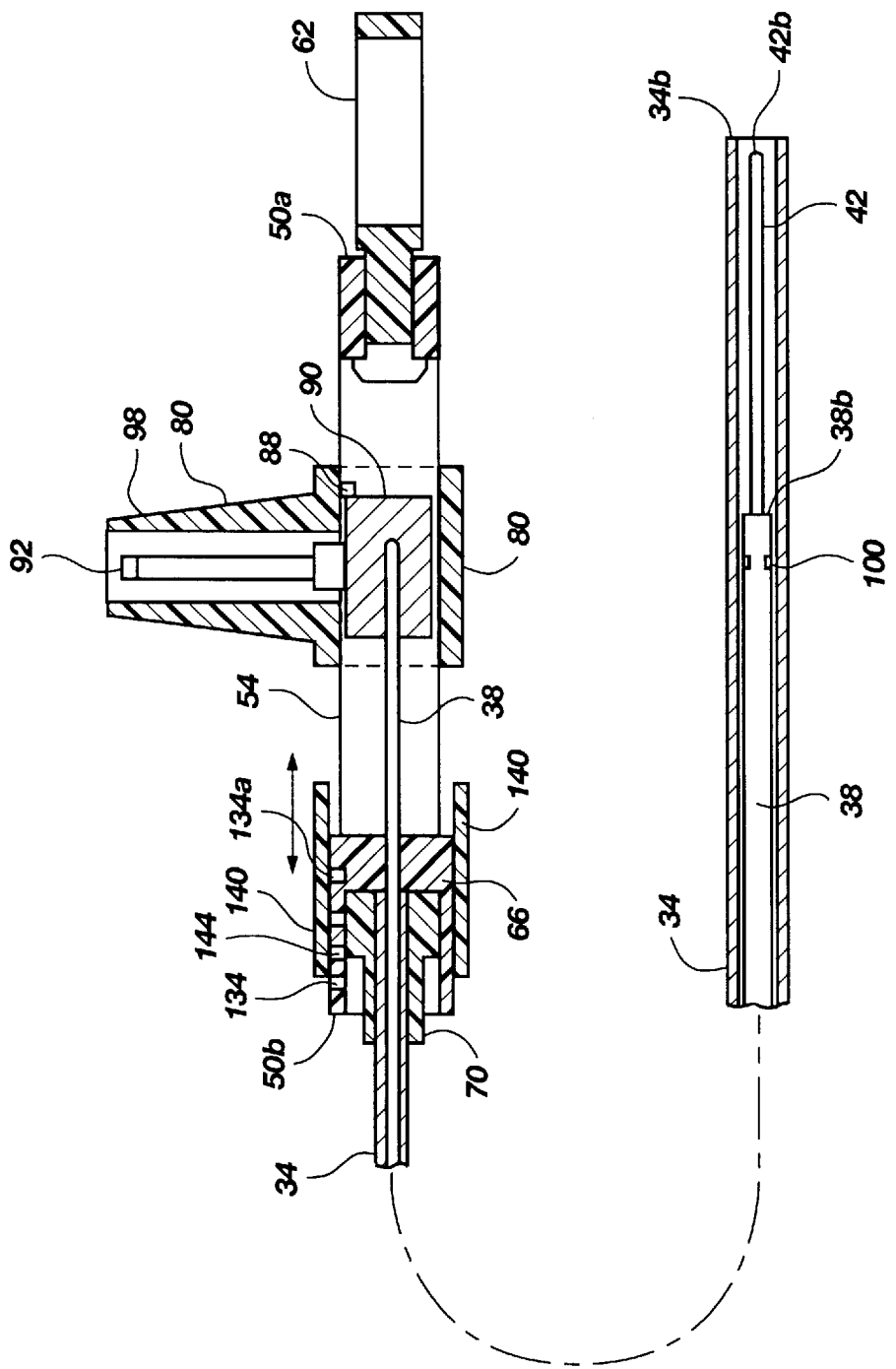
FIG. 4A shows a side cross-sectional view of the needle-knife actuation assembly shown in FIG. 4 with the extension regulator disposed on the body of the actuator assembly.

FIG. 4A shows a side cross-sectional view of the deployment mechanism 30 of a needle-knife actuation assembly shown in FIG. 4. The slidable stop 140 forming the extension regulator is disposed on the body 50 so that it is between a first, extreme proximal position wherein the slidable stop 140 would stop any extension of the needle-knife 42 outside the sheath 34, and a second, extreme distal position wherein the slidable stop would allow complete extension of the needle-knife.

Figure 5A:
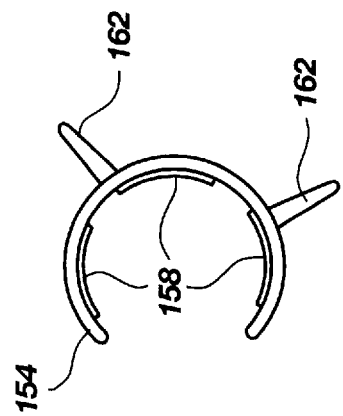
FIG. 5 is a top view of deployment mechanism similar to that shown in the previous figures, but having a plurality of grooves in the end portion, and an extension regulator configured to engagement with the end portion.
Figure 5:
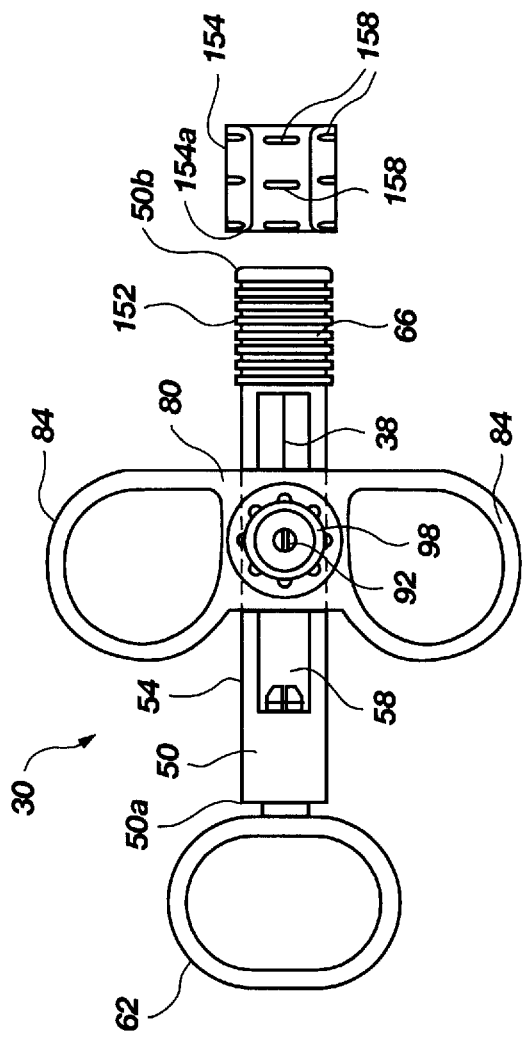

Referring to FIG. 5, there is shown an exploded view of yet another embodiment of the present invention. The deployment mechanism 30 is substantially the same as those discussed in preceding embodiments and is numbered accordingly. The primary difference between the deployment mechanism 30 of FIG. 5 is that a plurality of grooves 152 are formed in the body 50 in the end portion 66.

Also shown in FIG. 5 is an extension regulator 154 in the form of a generally C-shaped clip. The extension regulator 154 has a plurality of raised ribs 158 which are configured to mate within the grooves 152 in the end portion 66 of the body 50. The grooves 152 and ribs 158 are preferably small enough to allow relatively fine adjustments in where the extension regulator 154 is positioned. By controlling the location of a proximal end 154a of the extension regulator 154, the distal movement of the sliding member 80 can be limited to a third, desired position. Limiting the distal movement of the sliding member 80 thus limits the extension of a needle-knife or some other extendable and retractable medical instrument disposed in a catheter.

Turning now to FIG. 5A, there is shown an end view of the extension regulator 154. As was mentioned previously, the extension regulator 154 is formed by a generally C-shaped body having a plurality of protruding ribs 158 which are used to engage the grooves 152 on the body 50 of the deployment device 30. A pair of tabs 162 extend outwardly from the C-shaped body of the extension regulator 154. Squeezing the tabs 162 together deflects the C-shaped body outwardly and enables the protruding ribs 158 to be removed easily from the grooves 152. The extension regulator 154 can then be moved to a new location and the tabs 162 released, thereby locking the extension regulator in new desired position.

Figure 6:
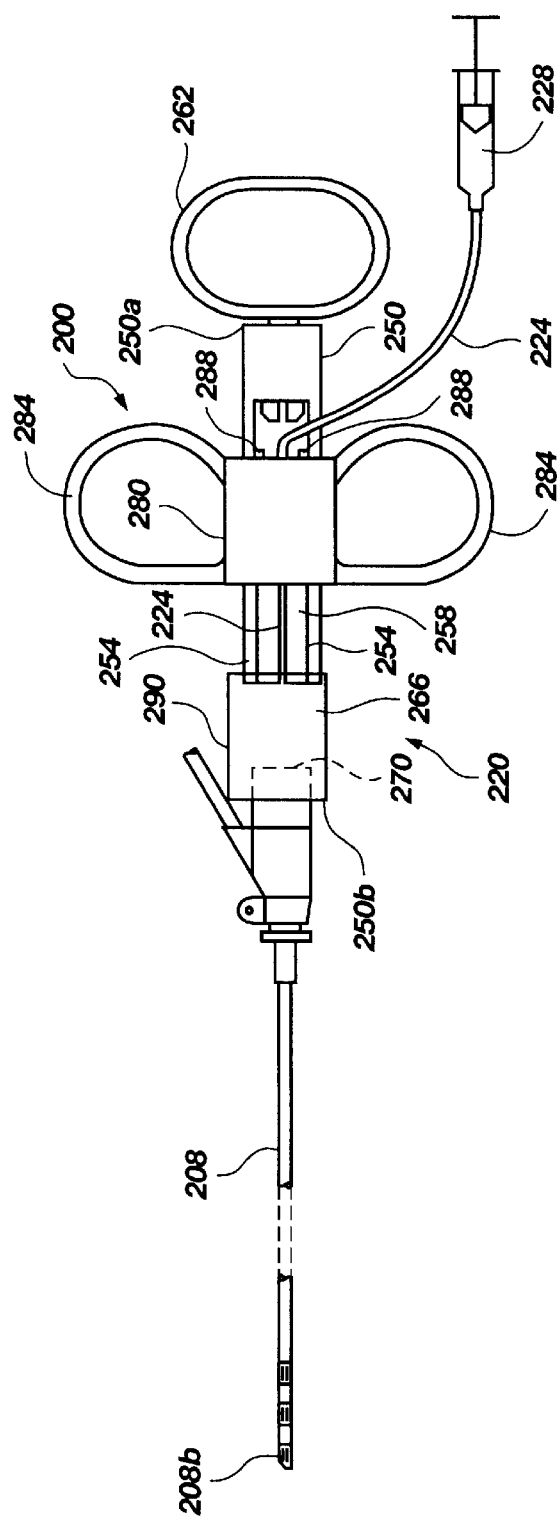
FIG. 6 is a top plan view of a deployment mechanism for a catheter carried injection needle, the extension of which is controlled by an extension regulator in accordance with the present invention.
Figure 6A:
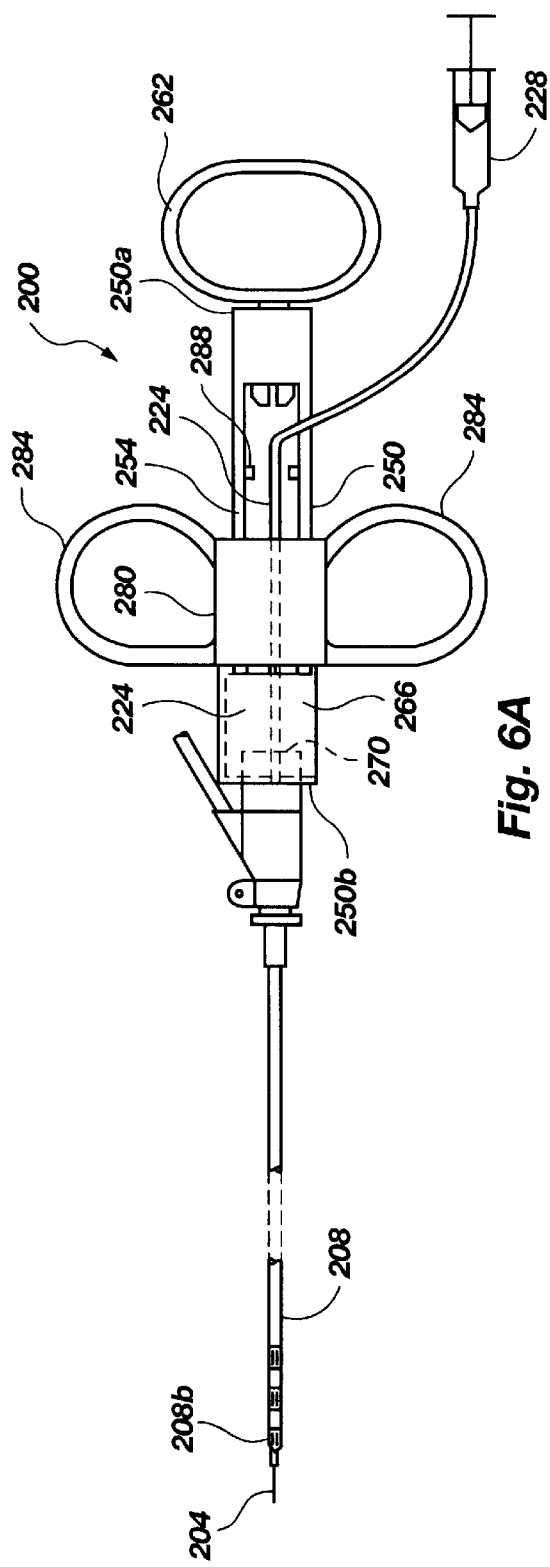
FIG. 6A is a top plan view of the deployment mechanism of FIG. 6 with the mechanism positioned to deploy the injection needle.

Turning now to FIGS. 6 and 6A, there is shown a top, plan view of an actuation assembly, generally indicated at 200, for a controlling extension of an injection needle 204 from the distal end 208b of a catheter 208 in which the injection needle is carried. While the discussion above has focussed primarily on the difficulties of using an electro-surgical instrument such as a needle-knife, the proper extension of injection needles out of the catheter is also a significant problem. The needle may be used, for example, to inject a chemotherapy drug into a tumor, or to apply medication to a particular location without having to subject the remainder of the patient's body to the drug.

Typically when an injection needle 204 is used, the physician advances the needle out of the catheter so that the needle-tip penetrates the desired object. A syringe is then used to inject a fluid through the needle. Requiring the physician to repeatedly move the injection needle by manipulation of the catheter or a sheath can be cumbersome and can slow the rate of the procedure. If a deployment device were provided, the user could deploy the injection needle whenever desired, and then retract the needle without having to move the entire needle assembly with respect to the catheter.

The actuator assembly 200 includes a deployment mechanism 220 and an elongated injection tube 224 for connecting the injection needle 204 to a syringe 228. As with the apparatus shown in FIG. 1 through FIG. 4A, the deployment mechanism 220 includes an elongate body 250. The elongate body 250 has a pair of rails 254 which are configured to define a centrally disposed slot 258. Body 250 also includes a first, proximal end 250a with a thumb ring 262 attached thereto, and a second, distal end 250b having an end portion 266 at which a fitting 270 is located for receiving the injection tube 224. A sliding member 280 is slidably connected to the body 250. The sliding member 280 preferably includes a pair of opposed finger rings 284 which enable a user to grasp the same between two fingers, typically the forefinger and index finger. By placing a thumb through thumb ring 262, the sliding member 280 may be advanced towards the second end 250b of the body 250. As the sliding member 280 moves, it pushes the injection tube 224 forward and thereby deploys the injection needle 204. The sliding member 280 may also be freely moved away from the second end 250b of the body 250 until the sliding member contacts a pair of stops 288 disposed along the rails 254, thereby withdrawing the injection needle 204 into the catheter 208.

In order to limit the distal movement of the sliding member 280, and thereby limit the extension of the injection needle 204 beyond the catheter 208, an extension regulator 290 is disposed on the deployment mechanism 220. The extension regulator 290 is moveable between a first, extreme proximal position, in which the extension regulator prevents distal movement of the sliding member 280, and a second, extreme distal position, in which the extension regulator does not interfere with distal movement of the sliding member.

Unlike most of the embodiments discussed above, the extension regulator is a cylindrical housing having threads on an inner wall thereof to threadedly engage the end portion 266. To adjust the position of the extension regulator 290, the extension regulator is rotated. If rotated in a first direction, the extension regulator 290 moves generally proximally and eventually reaches the first, extreme proximal position wherein the extension regulator prevents distal movement of the sliding member 280. If the extension regulator 290 is rotated in the opposite direction, the extension regulator moves toward the second, extreme distal position wherein it provides no interference to the movement of the sliding member 280. Between the two, the extension regulator defines a third position to control the amount of extension of the injection needle 204.

Figure 6B:
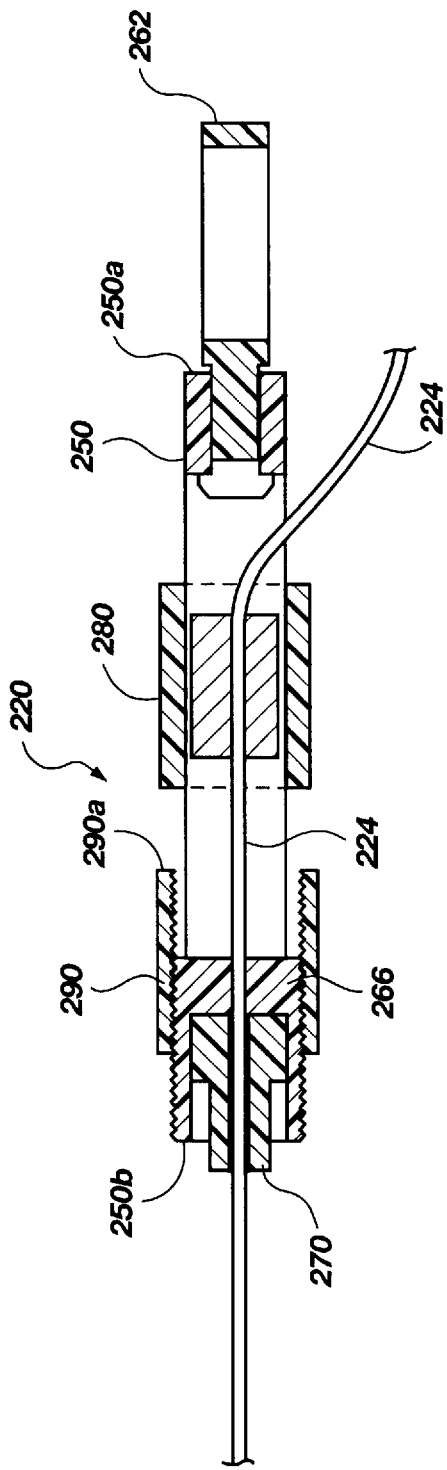
FIG. 6B is a cross-sectional view of the deployment mechanism and catheter of FIG. 6.

Referring to FIG. 6B1, there is shown a side cross-sectional view of the deployment device 220. The extension regulator 290 has been rotated so that a proximal end 290a thereof is disposed at a third position, between the first and second positions, to thereby stop the distal movement of the sliding member 280. By controlling the distal movement of the sliding member 280, the extension regulator limits the extent to which the injection needle 204 may be advanced out of the catheter. Thus, the physician is able to better control the injection needle 204 and obtain desired needle placement.

Referring now to FIG. 7, there is shown top view of the deployment mechanism 30 and an alternate embodiment of an extension regulator 170, made in accordance with the present invention. The deployment mechanism 30 is substantially the same as that described with respect to FIGS. 1 through 5A and is numbered accordingly. The only difference between the deployment mechanism 30 and those discussed with respect to FIGS. 1 through 5A is that the end portion 66 of the body 50 has helical threads 174 which circumscribe the end portion.

The extension regulator 170, in contrast, is significantly different than those discussed above. Namely, the extension regulator 170 is configured to enable selective movement thereof by sliding, ratcheting, and/or rotation of the extension regulator into the desired position. These various mechanisms are accomplished by a C-shaped housing 178, the interior of which is unthreaded, and a ratcheting flange 182 which is pivotably connected to the housing 178 so that the housing and the flange form a substantially cylindrical body. The flange 182 has threads 186 which engage the helical threads 174 of the end portion 66 to enable the position of the extension regulator 170 to be adjusted by rotating the housing 178 about the end portion. The flange 182 also is spring-loaded and the threads 186 on the flange and the threads 174 on the end portion 66 will interact to permit sliding of the extension regulator 170 in one direction with relative ease, while inhibiting sliding of the extension regulator 170 in the opposite direction. Furthermore, the flange 182 may be pivoted so that the threads 186 are no longer in engagement with the threads 174 of the end portion 66 to facilitate rapid movement of the extension regulator in either direction.

Referring now to FIG. 7A, there is shown a close-up view of the extension regulator 170 disposed about the end portion 66 of the body 50 of the deployment mechanism 30, the remainder of which is not shown. The end portion 66 is provided with a plurality of threads 174 which are disposed helically. The threads 174 have two faces which are at significantly different slopes. In particular, the threads 174 have a first, proximal face 174a which is disposed at a steep angle, such as 70 or 80 degrees. The threads 174 also have a second, distal face 174b which is disposed at a much lesser angle, such as 30 degrees.

The flange 182 is the only portion of the extension regulator 170 which is threaded. Like the threads 174 on the end portion 66, one face of the threads 186 of the extension regulator 170 has a steep angle, while the opposing face has a much more gradual slope. On the flange 182, however, the gradual slope (i.e. about 30 degrees) is disposed on the first, proximal face 186a so that it engages the gradual slope of the second, distal face 174b of the threads 174 on the end portion 66. Likewise, the second, distal face 186b of the threads 186 on the flange 182 are steeply angled (i.e. 70 to 80 degrees) and engage the steeply angled proximal face 174a of the threads 174 of the end portion 66.

The gradual slopes of the first, proximal face 186a of the flange 182 and the second, distal face 174b of the end portion 66 enable these two faces to slide with respect to each other. Thus, application of force to the extension regulator 170 in a proximal direction, as indicated by arrow 190, causes the flange 182 to be deflected upwardly a small amount. The deflection of the flange 182 enables the extension regulator 170 to slide proximally the distance of 1 thread, as shown in FIG. 7B. Once proximal face 186a of the threads 186 of the flange 182 and the distal face 174b of the threads 174 of the end portion 66 are no longer in contact, the spring 192 will force the threads 186 of the flange into a mating engagement with the threads 174 of the end portion 66, the extension regulator 170 having advanced the distance of one thread. By applying a small amount of pressure, the extension regulator can thus be ratcheted in a proximal direction and into engagement with the slide member 80.

While the extension regulator can be ratcheted in the proximal direction, it generally cannot be ratcheted in the distal direction. The steeply angled distal faces 186b of the threads 186 of the flange 182 engage the steeply angled proximal faces 174a of the threads 174 of the end portion 66. The steep faces provide significant resistance to horizontal movement in the distal direction. Thus, while the flange 182 is disposed in the position shown in FIG. 7A, the only feasible mechanism for distal movement of the extension regulator 170 is to rotate it in the proper direction.

Despite the above, rapid movement of the extension regulator in the distal direction is not impossible. Referring to FIG. 7C, the is shown a cross-sectional view of the end portion 66 and the extension regulator 170. The flange 182 has been pivoted so that its threads 186 are no longer engaged with the threads 174 of the end portion 66. Because the housing 178 of the extension regulator 170 is not threaded, disengaging the threads 186 of the flange 182 from the threads 174 of the end portion 66 enables the extension regulator to slide freely in either direction. Once the flange 186 is returned to a horizontal position, as shown in the end view of FIG. 7D, the threads 186 of the flange 182 again engage the threads 174 of the end portion 66. With the threads 174 and 186 engaged, proximal movement of the extension regulator requires rotation or ratcheting of the regulator, while distal movement requires rotation in an opposite direction. In such manner, the embodiment shown in FIGS. 7 through 7D enables both rapid and precise control of the distance which the sliding member 80 may move distally.

Turning now to FIGS. 8 and 9, there are shown two additional applications of the present invention. Shown in FIG. 8 is a actuator assembly, generally indicated at 300, for controllably deploying a medical instrument, such as a biopsy device 304, which is disposed adjacent the distal end 308b of a catheter 308. The catheter 308 is attached at a proximal end 308a to a deployment mechanism 312 by a luer lock 314.

The deployment mechanism 312 includes a base 320 in the form of a generally hollow body 324 with a pair of finger rings 328. A sliding member 332 in the form of a plunger is slidable between a first, extended, proximal position and a second, inserted, distal position. The sliding member 332 is attached to the biopsy device 304 by an elongate connector 336 which extends through a lumen of the catheter 308. With the sliding member 332 disposed in the proximal position, as shown in FIG. 8, the biopsy device will be withdrawn in the catheter 308. (In FIG. 8 the biopsy device is extended despite the position of the sliding member 332 simply show the extent to which it will typically extend from the catheter).

Disposed along the sliding member 332 are a plurality of stops 338. The stops 338 are staggered in a helical pattern about the sliding member 332 and are sufficiently small that they can slide into the base 320. A blocking wall 340 is disposed on one side of the base 320 so that the distal movement of the plunger is stopped when one of the stops 338 contacts the wall. By rotating the sliding member 332, the user can select which of the stops 338 contacts the blocking wall 340. Thus, if the user desires for the biopsy device 304 to extend only a small distance out of the sheath, the plunger is rotated so that stop 338a contacts the wall 340 when the sliding member is moved distally. If full extension is desired, the sliding member 332 is rotated so that the stop 338c contacts the wall. An intermediate position is provided by stop 338b.

Rotation of the sliding member 332 does not create torque in the connector 336 or otherwise interfere with its operation. The connector 336 is nested in the rotatable attachment 342 which connects the thumb ring 344 to the sliding member 332. As the sliding member rotates, the thumb ring 344 can be held stable, thereby preventing torque in the connector 336.

Thus, by rotation of the sliding member 332, the user is able to limit the distal range of motion of the sliding member to a third, desired position. Limiting the distal movement of the sliding member 332 limits the distance which the biopsy device 304 can extend from the catheter 308, thereby providing the physician with improved control over deployment of the biopsy device. While only three stops 338 are shown in FIG. 8, numerous stops could be used to provide a greater number of stopping locations.

Finally, FIG. 9 shows an embodiment which is somewhat to that shown in FIG. 8. The deployment mechanism 312 is used for activation of a bow-knife 384 disposed at the distal end 308'b of the catheter. The use of a bow-knife is typically for purposes similar to those which use a needle-knife, namely incising tissue. In the process of incising the tissue, it is important to control the distance which the electro-surgical elements 386 extends outwardly from the catheter. With respect to the deployment mechanism, most aspects of the deployment mechanism 312 are the same as discussed with respect to FIG. 8 and are therefore numbered accordingly. A binding post 390 similar to those discussed with respect to the needle-knife is provided on the sliding member 388.

Additionally, it should be appreciated that the deployment mechanism 312 is used in the exact opposite manner with a bow-knife. To extend the electro-surgical element outwardly from the distal portion of the catheter 308', the electro-surgical element is moved proximally. This causes the distal end 308'b of the catheter to bow and thereby spaces the element from the catheter for cutting. Thus, rather than limiting distal movement of the sliding member 388, the extension regulator of this embodiment actually limits withdrawal of the sliding member from the base.

One primary difference between the sliding members of the embodiments is that the sliding member 388 of FIG. 9 does not rotate. Rather, a plurality of spring-loaded stops 348 are disposed in one of the rails 350 of the sliding member 388. Each stop 348 is attached to a control button 354. Pressing the control button 354 of a particular stop 348 releases the stop so that it extends outwardly from the sliding member 388 as indicated at stop 348*a*. The distance which the stop 348*a* extends beyond the rail 350 is sufficient to prevent the any portion of the sliding member 388 distal thereto from leaving the base 320. By selecting which control button 354 is depressed, the user can limit the ability of the sliding member 388 to advance proximally out of the base 320 and thereby control the bow-knife 384 at the distal end 308'*b* of the catheter 308'. As will be apparent to those skilled in the art, there are numerous different methods for releasing the stop. Preferably, the method used will enable the user to return the stop 348 to its original position. In such a manner, the accidental release of a stop 348 will not interfere with continued use of the deployment mechanism 312.

Thus there is disclosed an improved apparatus and method for controlling the extension of a medical device from a catheter. The medical device which may be so controlled can include virtually any medical instrument which can be deployed from and retracted into the distal end of the catheter. In such a manner, physicians and other medical professionals can be relieved from the guess work which is commonly associated with deployment of medical instruments from catheters, and accidental lacerations, incisions and other damage to ducts should be reduced.

Those skilled in the art will appreciate numerous modifications which can be made to any of the embodiments described herein without departing from the scope and spirit of the present invention. The appended claims are intended to cover such modifications.

What is claimed is:

1. A apparatus for selectively deploying a medical instrument, the apparatus comprising:

an elongate catheter having a proximal end and a distal end;

a medical instrument having a retracted position wherein the medical instrument is disposed within the distal end of the catheter, and an extended position wherein the medical instrument is at least partially extended from the catheter;

deployment means attached to the proximal end of the catheter for selectively extending and retracting the medical instrument, the deployment means comprising a sliding member disposed in mechanical communication with the medical instrument for moving the medical instrument between the extended and retracted positions, the sliding member being slidable between a first, proximal position, wherein the medical instrument is disposed in the retracted position, and a second, distal position, wherein the medical instrument is disposed in the extended position; and regulator means connected to the deployment means for stopping the sliding member at a third position between the first, proximal position and the second, distal position, to thereby limit the extension of the medical instrument from the catheter.

2. The apparatus of claim 1, wherein the deployment means comprises an elongate body, the slidable member being slidable along said body between the first, proximal position and the second, distal position, and wherein the regulator means is disposed on the elongate body to thereby prevent sliding of the sliding member into the second, distal position.

3. The apparatus of claim 2, wherein the regulator means comprises a stop disposed in frictional engagement with the elongate body.

4. The apparatus of claim 2, wherein elongate body has a post extending outwardly therefrom, and wherein the regulator means comprises a housing having a plurality of channels formed therein for selectively engaging the channels to thereby control the position of said housing with respect to the post.

5. The apparatus of claim 4, wherein the channels in the housing are interconnected so as to facilitate movement of the post between the channels.

6. The apparatus of claim 5, wherein the housing has a central channel extending substantially parallel to the elongate body, and a plurality of channels extending laterally from the central channel.

7. The apparatus of claim 6, wherein the channels extending laterally from the central channel are disposed in a staggered configuration to thereby enable incremental adjustment of the housing with respect to the post.

8. The apparatus of claim 6, wherein the plurality of channels extending laterally from the central channel extend laterally and proximally so as to be sloped relative to the central channel.

9. The apparatus of claim 6, wherein at least one of the plurality of channels is disposed such that when the post is within said at least one channel, the medical instrument is held in the retracted position.

10. The apparatus of claim 4, wherein the plurality of channels includes at least one channel disposed transverse to the elongate body and having an end, such that movement of the housing in a distal direction along the elongate body moves housing until the post engages the end of the at least one channel to thereby prevent further distal movement of the housing.

11. The apparatus of claim 2, wherein regulator means comprises a housing with a post extending inwardly therefrom, and wherein the elongate body has a plurality of channels formed therein and configured for nestably receiving the post of the regulator means to thereby control the position of said housing with respect to the elongate body.

12. The apparatus of claim 11, wherein the channels in the elongate body are interconnected so as to facilitate movement of the post between the channels.

13. The apparatus of claim 11, wherein the plurality of channels includes at least one channel disposed transverse to the elongate body and having an end, such that movement of the housing in a distal direction along the elongate body moves housing until the post engages the end of the at least one channel to thereby prevent further distal movement of the housing.

14. The apparatus of claim 1, wherein deployment means includes an elongate body having a threaded portion, and wherein the regulator means comprises a housing and a threaded engagement means for engaging the threaded portion of the elongate body such that rotation of the housing in one direction moves the housing distally along the threaded portion of the elongate body, and rotation the housing in an opposing direction moves the housing proximally along the threaded portion of the elongate body.

15. The apparatus of claim 14, wherein the housing has an inner wall and wherein the threaded engagement means is formed on the inner wall of the housing.

16. The apparatus of claim 15, wherein the threaded engagement means is pivotably attached to the housing, the threaded engagement means being pivotable into and out of engagement with the threaded portion of the elongate body while the housing remains disposed about the threaded portion.

17. The apparatus of claim 16, wherein the housing and threaded engagement means is attached to the housing and the housing is configured such that when the threaded engagement means is disposed so as to be out of engagement with the threaded portion of the elongate body, the housing is able to slide along the threaded portion.

18. The apparatus of claim 14, wherein the threaded portion of the elongate body comprises helically wound threads, each thread having a first face and a second face, the first face having a steep slope and the second face has a gradual slope, and wherein the threaded engagement means comprises a plurality of threads having a first face and a second face, the first face having a gradual slope and engaging the second face of the threads of the threaded portion, and the second face having a steep slope and engaging the first face of the threads of the threaded portion.

19. The apparatus of claim 18, wherein the threaded engagement means slides over the threaded portion of the elongate housing when force is applied to the housing in a first direction, wherein the forces moves the second face of the threaded engagement means away from an adjacent first face of the threaded portion of the elongate body, but will not slide over the threaded portion of the elongate housing when force is applied to the housing so as to force the second face of the threads of the threaded engagement means into contact with and adjacent first face of the threads of the threaded end portion.

20. The apparatus of claim 1, wherein deployment means includes a base, and wherein at least a portion of the sliding member is slidable into and out of the base.

21. The apparatus of claim 20, wherein the regulator means comprises means for limiting the portion of the sliding member which can slide into the base.

22. The apparatus of claim 21, wherein the regulator means comprises a plurality of stops disposed on the sliding member so as to engage the blocking member to thereby prevent further sliding of the sliding member.

23. The apparatus of claim 22, wherein the sliding member is rotatable, and wherein the stops are disposed about the sliding member such that rotation of the sliding member determines which stop engages the blocking member, and thereby determines the extend to which the sliding member may be slid into the base.

24. The apparatus of claim 21, wherein at least one stop is disposed on the sliding member, the stop being moveable between a first position, wherein the stop does not prevent further advance of the sliding member into the base, and a second portion wherein the stop prevents further advance of the sliding member into the base.

25. The apparatus of claim 24, further comprising actuation means for moving the stop from the first position to the second position.

26. The apparatus of claim 1, wherein the medical instrument comprises a needle-knife, and wherein the needle knife is disposable in communication with a means for conducting current to the needle-knife.

27. The apparatus of claim 1, wherein the medical instrument comprises an injection needle, and wherein the injection needle is disposed in communication with a syringe.

28. The apparatus of claim 1, wherein the medical instrument comprises a biopsy device.

29. An apparatus for controlling deployment of a medical instrument disposed at the distal end of a catheter, the apparatus comprising:
  a deployment mechanism attachable to the medical instrument and to the catheter, the deployment mechanism including:
    an elongate body; and
    a sliding member disposed on the elongate body and slidable therealong between a first, proximal position and a second distal direction, the sliding member being disposable in mechanical communication with the medical instrument such that distal movement of the slidable member moves the medical instrument away from the distal end of the catheter; and
  regulator means disposed along the elongate body of the deployment mechanism for selectively inhibiting distal movement of the sliding member along the elongate body.

30. The apparatus of claim 29, wherein the regulator means comprises a housing disposed about the elongate body and disposed in frictional engagement with the elongate body.

31. The apparatus of claim 30, wherein the housing includes a friction layer formed thereon for engaging the elongate body, to thereby resist sliding along the elongate body.

32. The apparatus of claim 29, wherein the regulator means comprises a stop having at least one channel formed therein, and wherein a post extends outwardly from the elongate body and into the at least one channel to nest within the at least one channel and selectively prevent sliding of the stop.

33. The apparatus of claim 32, wherein the at least one channel comprises a plurality of interconnected channels, the post being moveable between said plurality of interconnecting channels to selectively prevent movement of the stop.

34. The apparatus of claim 29, wherein the elongate body has a plurality of channels formed there, and wherein the regulator means comprises a housing slidable along the elongate body, the housing having a post extending inwardly therefrom so as to nest in the channels in the elongate body and there selectively inhibit movement of the stop.

35. The apparatus of claim 29, wherein the elongate body has a threaded portion, and wherein the regulator means comprises a stop having a threaded portion for engaging the threaded portion of the regulator means such that rotation of the stop moves the stop linearly along the elongate body.

36. The apparatus of claim 35, wherein the stop comprises a housing having a threaded inner portion for engaging the threaded portion of the elongate body.

37. The apparatus of claim 35, wherein the stop comprises a housing having an unthreaded inner wall, and a flange adjustable attached to the housing, the flange having a threaded portion for engaging the threaded portion of the elongate body.

38. The apparatus of claim 37, wherein the flange is pivotably attached to the housing and configured so that the threaded portion of the flange may be pivoted out of engagement with the threaded portion of the elongate body, to thereby permit proximal and distal sliding of the housing relative to the threaded portion of the elongate body.

39. An apparatus for controlling deployment of a medical instrument disposed at the distal end of a catheter, the apparatus comprising:
  a deployment mechanism attachable to the medical instrument and to the catheter, the deployment mechanism including:
    an base; and
    a sliding member disposed in slidable engagement with the base and movable between a first, proximal position and a second distal direction, the sliding member being disposable in mechanical communication with the medical instrument such that movement of the slidable member in one direction moves the medical instrument away from the distal end of the catheter and movement in the opposite direction moves the medical instrument toward the distal end of the catheter; and regulator means disposed along sliding member for selectively inhibiting movement of the sliding member in one direction respect to the base, so as to thereby selectively limit the movement of the medical instrument away the catheter adjacent the distal end thereof.

40. The apparatus of claim 39, wherein the regulator means comprises a plurality of stops disposed on the sliding member to thereby limit movement of the sliding member with respect to the base.

41. The apparatus of claim 40, wherein the sliding member is rotatable, and wherein the stops are disposed about the sliding member in a spaced array, such that rotation of the sliding member controls the extent to which the stops limit sliding movement of the sliding member with respect to the base.

42. The apparatus of claim 40, wherein the apparatus further includes a catheter attached to the deployment mechanism, the medical instrument extending from the distal end of the catheter, and wherein the sliding member is movable in a distal direction to thereby extend the medical instrument from the distal end of the catheter.

43. The apparatus of claim 42, wherein the stops are disposed so as to selectively limit the distal movement of the sliding member, and thereby limit the distal movement of the medical instrument.

44. The apparatus of claim 39, wherein the deployment mechanism further includes a catheter, the medical instrument extending from the catheter adjacent the distal end, and wherein the sliding member is movable in a proximal direction to thereby bow the distal end of the catheter and dispose a portion of the extend the medical instrument more distant from the catheter.

45. An apparatus for selectively deploying a medical instrument, the apparatus comprising:

an elongate catheter having a proximal end and a distal end;

a electro-surgical element disposed in the catheter and slidable relative thereto, the electro-surgical element having a distal portion being moveable between an extended and retracted position;

deployment means attached to the proximal end of the catheter for selectively extending and retracting the distal portion of the electro-surgical element, the deployment means comprising a sliding member disposed in mechanical communication with the electro-surgical element for moving the distal portion of the electro-surgical element between the extended and retracted positions, the sliding member being slidable between a first position, wherein the electro-surgical element is disposed in the retracted position, and a second position, wherein the electro-surgical element is disposed in the extended position; and regulator means connected to the deployment means for limiting sliding of the sliding member toward the second position, to thereby limit the extension of the electro-surgical element from the catheter.

46. The apparatus of claim 45, wherein the electro-surgical element is a needle-knife which is extendable from and retractable into the distal end of the catheter, and wherein the regulator means is disposed to limit movement of the sliding member in a distal direction with respect to the deployment means.

47. The apparatus of claim 45, wherein the electro-surgical instrument extends from the catheter at a point adjacent the distal end and attaches to the catheter distally from the point at which the instrument extends from the catheter to thereby have a continuously exposed portion of the electro-surgical element.

48. The apparatus of claim 47, wherein movement of the sliding member proximally with respect to the deployment means bends the distal end of the catheter and thereby extends the exposed portion of the electro-surgical element from the distal end of the catheter.

* * * * *